US012625146B2

(12) United States Patent
Georgopoulou et al.

(10) Patent No.: US 12,625,146 B2
(45) Date of Patent: May 12, 2026

(54) S100A8 AS BLOOD BIOMARKER FOR THE NON-INVASIVE DIAGNOSIS OF ENDOMETRIOSIS

(71) Applicant: Roche Diagnostics Operations, Inc., Indianapolis, IN (US)

(72) Inventors: Aikaterini Georgopoulou, Lucerne (CH); Martin Hund, Horw (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 969 days.

(21) Appl. No.: 17/575,176

(22) Filed: Jan. 13, 2022

(65) Prior Publication Data

US 2022/0137068 A1      May 5, 2022

Related U.S. Application Data

(63) Continuation of application No. PCT/EP2020/070427, filed on Jul. 20, 2020.

(30) Foreign Application Priority Data

Jul. 22, 2019    (EP) ..................................... 19187474

(51) Int. Cl.
*G01N 33/68*        (2006.01)

(52) U.S. Cl.
CPC ... *G01N 33/6893* (2013.01); *G01N 2800/364* (2013.01)

(58) Field of Classification Search
None
See application file for complete search history.

(56) References Cited

U.S. PATENT DOCUMENTS

| | | | |
|---|---|---|---|
| 5,221,605 A | 6/1993 | Bard et al. | |
| 5,316,757 A | 5/1994 | Sherry et al. | |
| 5,342,606 A | 8/1994 | Sherry et al. | |
| 5,385,893 A | 1/1995 | Kiefer | |
| 5,428,139 A | 6/1995 | Kiefer et al. | |
| 5,428,155 A | 6/1995 | Sherry et al. | |
| 5,462,725 A | 10/1995 | Kiefer et al. | |
| 5,480,990 A | 1/1996 | Kiefer et al. | |
| 5,591,581 A | 1/1997 | Massey et al. | |
| 5,597,910 A | 1/1997 | Gudibande et al. | |
| 5,679,519 A | 10/1997 | Oprandy | |
| 5,739,294 A | 4/1998 | Kiefer et al. | |
| 5,750,660 A | 5/1998 | Kiefer et al. | |
| 5,834,461 A | 11/1998 | Albright et al. | |
| 2007/0087386 A1* | 4/2007 | Yang .................. | G01N 33/6893 435/7.1 |
| 2008/0318237 A1 | 12/2008 | Giudice | |
| 2010/0111861 A1 | 5/2010 | Liu et al. | |
| 2010/0120064 A1* | 5/2010 | Aoki ..................... | C07K 16/28 435/7.9 |
| 2012/0028268 A1* | 2/2012 | Kentsis .............. | G01N 33/6893 435/7.1 |
| 2014/0227725 A1* | 8/2014 | Fagerhol .......... | G01N 33/57488 436/501 |
| 2018/0017576 A1* | 1/2018 | Roth ...................... | G01N 33/96 |

FOREIGN PATENT DOCUMENTS

| | | | |
|---|---|---|---|
| CN | 112334776 A | 2/2021 | |
| EP | 0488152 A2 | 6/1992 | |
| JP | 2002539802 A | 11/2002 | |
| WO | 8706706 A1 | 11/1987 | |
| WO | 9005296 A1 | 5/1990 | |
| WO | 9005301 A1 | 5/1990 | |
| WO | 9214139 A1 | 8/1992 | |
| WO | 9508644 A1 | 3/1995 | |
| WO | 9525882 A1 | 9/1995 | |
| WO | 9606946 A1 | 3/1996 | |
| WO | 9624690 A1 | 8/1996 | |
| WO | 9633411 A1 | 10/1996 | |
| WO | 9635812 A1 | 11/1996 | |
| WO | 9639534 A1 | 12/1996 | |
| WO | 9640978 A1 | 12/1996 | |
| WO | 9641175 A1 | 12/1996 | |
| WO | 9733176 A1 | 9/1997 | |
| WO | 9812539 A1 | 3/1998 | |
| WO | 200056920 | 9/2000 | |
| WO | 2005012359 A2 | 2/2005 | |
| WO | WO-2009068254 A1 * | 6/2009 | .......... G01N 33/689 |
| WO | 2012107419 A1 | 8/2012 | |
| WO | 2015128671 A1 | 9/2015 | |
| WO | 2018044979 A1 | 3/2018 | |
| WO | 2019243391 A1 | 12/2019 | |
| WO | 2021013784 A1 | 1/2021 | |

OTHER PUBLICATIONS

Okada (Inflammation 2018 41:59-72). (Year: 2018).*
MBL category (Dec. 2012; total 2 pages). (Year: 2012).*
Alexei A. Koshkin et al., "LNA (Locked Nucleic Acid): An RNA Mimic Forming Exceedingly Stable LNA:LNA Duplexes", J. Am. Chem. Soc, vol. 120, pp. 13252-13253.
Nnoaham et al., Developing symptom-based predictive models of endometriosis as a clinical screening tool: results from a multicenter study: Endometriosis; Sep. 2012, vol. 98, No. 3, pp. 692-701.e5.
Naito et al., Usefulness of Serum CA 125 Levels in Diagnosis and Treatment of Endometriosis, IRYO, Dec. 1991, vol. 45. No. 12, pp. 1153-1158.

(Continued)

*Primary Examiner* — Changhwa J Cheu
(74) *Attorney, Agent, or Firm* — Taft Stettinius & Hollister LLP

(57) ABSTRACT

The present invention relates to methods of assessing whether a patient has endometriosis or is at risk of developing endometriosis, to methods of selecting a patient for therapy, and method of monitoring a patient suffering from endometriosis or being treated for endometriosis by determining the amount or concentration of S100A8 in a sample of the patient, and comparing the determined amount or concentration to a reference.

25 Claims, 5 Drawing Sheets

(56)                    References Cited

OTHER PUBLICATIONS

Figures 1A, 1B, 1C:
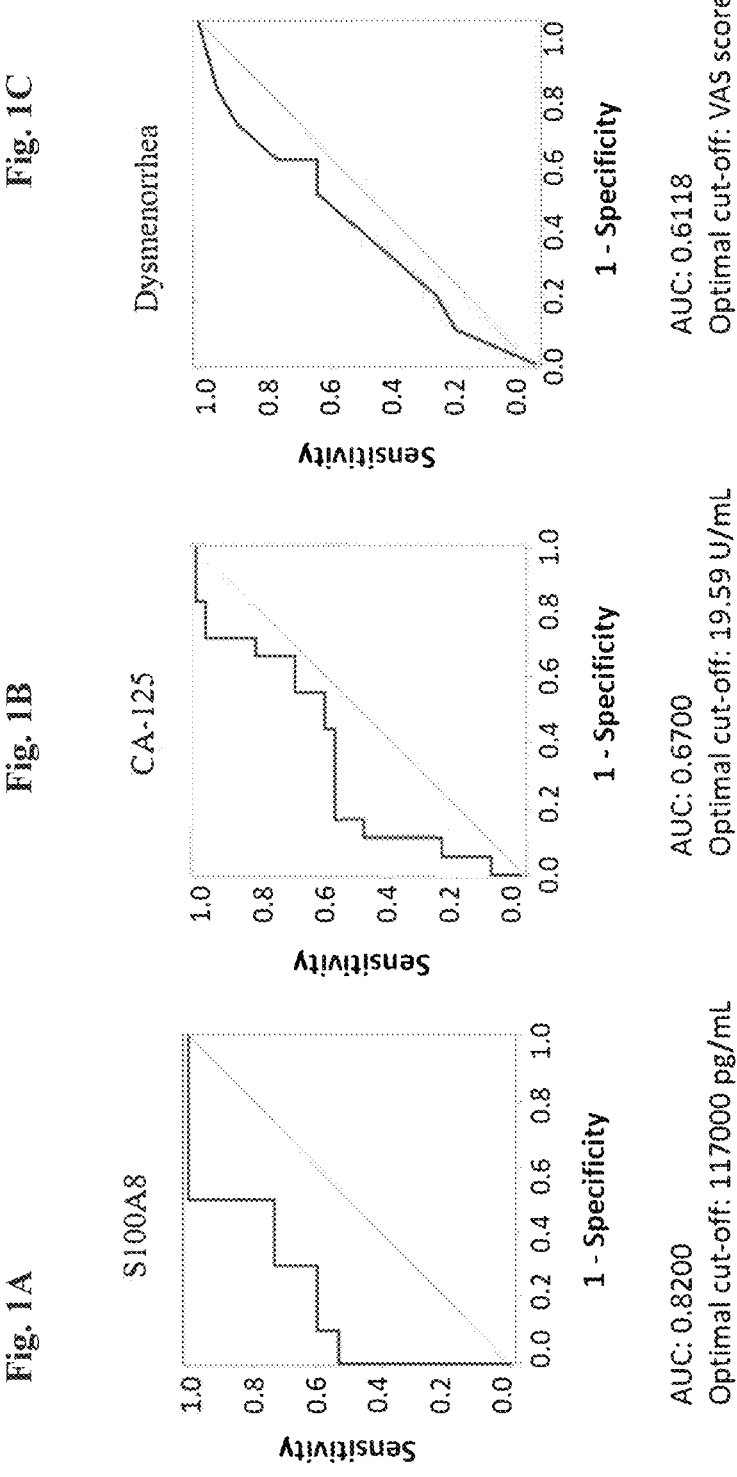

Wickstrom et al., Minimal Clinically important difference for pain on the VAS scale and he relation to quality of life in women with endometriosis; Clinical Trial; Sex Reproductive Healthcare; Oct. 2017, vol. 13, pp. 35-40.

Blend et al., Labeling anti-HER2/neu Monoclonal Antibodies with 111In and 90Y Using a Bifunctional DTPA Chelating Agent, Cancer Biotherapy & Radiopharmaceuticals 18 (2003) 355-363.

Briggs et al., "Synthesis of Functionalised Fluorescent Dyes and Their Coupling to Amines and Amino Acids," J. Chem. Soc., Perkin-Trans. 1 (1997) 1051-1058.

Camera et al., Comparative biodistribution of indium- and yttrium-labeled B3 monoclonal antibody conjugated to either 2-(p-SCN-Bz)-6-methyl-DTPA (1B4M-DTPA) or 2-(p-SCN-Bz)-1,4,7,10-tetraazacyclododecane tetraacetic acid (2B-Dota), J. Nucl. Med. 21 (1994) 640-646.

Camera et al., Evaluation of a new DTPA-derivative chelator: comparative biodistribution and imaging studies of 111In-labeled B3 monoclonal antibody in athymic mice bearing human epidermoid carcinoma xenografts, Nucl. Med. Biol. 20 (1993) 955-62.

Chen et al., Immunoglobulin D enhances immune surveillance by activating antimicrobial, proinflammatory and B cell-stimulating programs in basophils, (2009) Nat. Immunol. 10:889-898.

Cozzolino et al., Variables Associated with Endometriosis-related Pain: A Pilot Study using a Visual Analogue Scale, Rev Bras Ginecol Obstet 2019; 41(3) 170-175.

Deisenhofer, Crystallographic Refinement and Atomic Models of a Human Fc Fragment and Its Complex with Fragment B of Protein A from Staphylococcus aureus at 2.9- and 2.8-A Resolution, (1981) Biochemistry 20:2361-2370.

Denardo et al., Comparison of 1,4, 7 , 10-Tetraazacyclododecane-N,N', N' ', N'' '-tetraacetic acid (DOTA)-Peptide-ChL6, a Novel Immunoconjugate with Catabolizable Linker, to 2-Iminothiolane-2-fp-(Bromoacetamido )benzyl]-DOTA-ChL6 in Breast Cancer Xenografts1, Clinical Cancer Research 4 (1998) 2483-90.

Desmyter et al., Crystal structure of a camel single-domain VH antibody fragment in complex with lysozyme, (1996) Nat. Structure Biol. 3:803-811.

Dodeigne et al., Chemiluminescence as diagnostic tool. A review, Talanta 51 (2000) 415-439.

Geisberger et al., The riddle of the dual expression of IgM and IgD, (2006) Immunology 118:429-437.

Hnatowich et al., The Preparation of DTPA-Coupled Antibodies Radiolabeled with Metallic Radionuclides: an Improved Method, J. Immunol. Methods 65 (1983) 147-157.

Huston et al., Protein engineering of antibody binding sites: Recovery of specific activity in an anti-digoxin single-chain Fv analogue produced in *Escherichia coli*, (1988) Proc. Natl. Acad. Sci. USA 85, 5879-5883.

Izard et al., An Improved Method for Labeling Monoclonal Antibodies with Samarium-153: Use of the Bifunctional Chelate 2-(p-Isothiocyanatobenzyl)-6-methyldiethylenetriaminepentaacetic Acid, Bioconjugate Chem 3 (1992) 346-350.

Janeway et al., (2001) Immunobiology, Garland Science.

Kabat et al.: "Sequences of Proteins of Immunological Interest", 1991, Public Health Service, National Institutes of Health.

Knight et al., Occurrence, Mechanisms and Analytical Applications of Electrogenerated Chemiluminescence A Review, Analyst, 1994, 119: 879-890.

Kobayashi et al., Evaluation of the in Vivo Biodistribution of Indium-111 and Yttrium-88 Labeled Dendrimer-1B4M-DTPA and Its Conjugation with Anti-Tac Monoclonal Anitbody, Bioconjugate Chem. (1999) 103-111.

Kobayashi et al., Evaluation of the In Vivo Biodistribution of Yttrium-Labeled Isomers of CHX-DTPA-Conjugated Monoclonal Antibodies, J. Nucl. Med. 39 (1998) 829-36.

Kufer et al., A revival of bispecific antibodies, (2004) Trends Biotechnol. 22:238-244.

Kukis et al., Optimized Conditions for Chelation of Yttrium-90-DOTA Immunoconjugates, J. Nucl. Med. 39 (1998) 2105-2110.

Lee et al., Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts, Cancer Res. 61 (2001) 4474-4482.

Mardirossian et al., The stability in liver homogenates of indium-111 and yttrium-90 attached to antibody via two popular chelators, Nucl. Med. Biol. 20 (1993) 65-74.

Meares et al., Macrocyclic chelates of radiometals for diagnosis and therapy, J Cancer (1990), Suppl. 10:21-26.

Meares et al., Conjugation of Antibodies with Bifunctional Chelating Agents: Isothiocyanate and Bromoacetamide Reagents, Methods of Analysis, and Subsequent Addition of Metal Ions, Anal Biochem. 142 (1984) 68-78.

Miederer et al., Pharmacokinetics, Dosimetry, and Toxicity of the Targetable Atomic Generator, 225Ac-HuM195, in Nonhuman Primates, J. Nucl. Med. 45 (2004) 129-137.

Mirzadeh et al., Radiometal Labeling of Immunoproteins: Covalent Linkage of 2-(4-Isothiocyanatobenzyl) diethylenetriaminepentaacetic Acid Ligands to Immunoglobulin, Bioconjugate Chem 1(1990) 59-65.

Mitchell et al., Targeting Primary Human Ph+ B-Cell Precursor Leukemia-Engrafted SCID Mice Using Radiolabeled Anti-CD19 Monoclonal Antibodies, J. Nucl. Med. 44 (2003) 1105-1112.

Nikula et al., Alpha-Emitting Bismuth Cyclohexylbenzyl DTPA Constructs of Recombinant Humanized Anti-CD33 Antibodies: Pharmacokinetics, Bioactivity, Toxicity and Chemistry, J. Nucl. Med. 40 (1999) 166-76.

Nikula et al., A Rapid, Single Vessel Method for Preparation of Clinical Grade Ligand Conjugated Monoclonal Antibodies, Nucl. Med. Biol. 22 (1995) 387-90.

Schmidt et al., RAGE: A Multiligand Receptor Contributing to the Cellular Response in Diabetic Vasculopathy and Inflammation, Semin Thromb Hemost. 2000; 26(5):485-493.

Roselli et al., Cancer Biotherapy & Radiopharmaceuticals, 14 (1999) 209-20.

Ruegg et al., Cancer Res 50 (1990) 4221-4226.

Signorile et al., Serum Biomarker for Diagnosis of Endometriosis, J Cell Physiol 2014; 229-1731-1735.

Underdown et al., IMMUNOGLOBULIN A: Strategic Defense Initiative at the Mucosal Surface, (1986) Annu. Rev. Immunol. 4:389-417.

Verel et al., Quantitative 89Zr Immuno-PET for In Vivo Scouting of 90Y-Labeled Monoclonal Antibodies in Xenograft-Bearing Nude Mice, J. Nucl. Med. 44 (2003) 1663-1670.

Written Opinion of the International Searching Authority, European Patent Office, International Patent Application No. PCT/EP2020/070427, Oct. 7, 2020, 11 pages.

Ingersoll et al., Comparison of gene expression profiles between human and mouse monocyte subsets, Blood. 2010; 115(3): e10-9.

International Search Report, European Patent Office, International Patent Application No. PCT/EP2020/070427, Oct. 7, 2020, 5 pages.

International Preliminary Report on Patentability, The International Bureau of WIPO, International Patent Application No. PCT/EP2020/070427, Jan. 25, 2022, 10 pages.

Adamson et al., Creating solutions in endometriosis: global collaboration through the Wold Endometriosis Research Foundation; Journal of Endometriosis, 2010, vol. 2, No. 1, pp. 3-6.

Ahn et al., Immune-inflammation gene signatures in endometriosis patients; Fertil Steril., 2016, vol. 106, No. 6, pp. 1420-1431e7.

Bazot et al., Role of transvaginal sonography and magnetic resonance imaging int eh diagnosis of uterine adenomyosis; Fertility and Serility, 2018, vol. 109, No. 3, pp. 389-397.

Borner et al., Pain Mechanisms in Peritoneal Diseases Might Be Partially Regulated by Estrogen; Reprod Sci., 2018, vol. 25, No. 3, pp. 424-434.

Bokor et al., Density of small diameter sensory nerve fibres in endometrium: a semi-invasive diagnostic test for minimal to mild endometriosis; Human Reproduction, 2009, vol. 24, No. 12, pp. 3025-3032.

(56) References Cited

OTHER PUBLICATIONS

Burney et al., Gene Expression Analysis of Endometrium Reveals Progesterone Resistance and Candidate Susceptibility Genes in Women with Endometriosis; Endocrinology, 2007, vol. 148, No. 8, pp. 3814-3826.

Carter et al., Structure, Expression, and Some Regulatory Mechanisms of the Rat Preprotachykinin Gene Encoding Substance P, Neurokinin A, Neuropeptide K, and Neuropeptide Y; The Journal of Neuroscience, 1990, vol. 10, No. 7, pp. 2203-2214.

Chapron et al., Diagnosing adenomyosis: an integrated clinical and imaging approach; Human Reproduction Update, 2020, vol. 26, No. 3, pp. 392-411.

Cozzolino et al., Variables Associated with Endometriosis-related Pain: A Pilot Study using a Visual Analogue Scale; ORCID, 2018, 6-pages.

Ernst et al., Detection of stable N0erminal protachykinin A immunoreactivity in human plasma and cerebrospinal fluid; Peptides 29, 2008, pp. 1201-1206.

Eyster et al., Whole genome deoxyribonucleic acid microarray analysis of gene expression in ectopic versus eutopic endometrium; Endometriosis, Fertility and Sterility, 2007, vol. 88, No. 6, 29-pages.

Fadhlaoui et al., Endometriosis and infertility: how and when to treat? frontiers in Surgery, 2014, 6-pages.

Ferrero et al., Proeomic Analysis of Peritoneal Fluid in Women with Endometriosis; Journal of research articles Proteome research; 2007, vol. 6, pp. 3402-3411.

Ferrero et al., Peritoneal fluid proteome in women with different ASRM stages of endometriosis; Gynecological Endocrinology, 2008, vol. 24, No. 1, pp. 433-441.

Ferrero et al., GnRH Analogue Remarkably Down-Regulates Inflammatory Proteins in Peritoneal Fluid Proeome of Women with Endometriosis; The Journal of Reproductive Medicine; 2009, 9-pages.

Foell et al., Phagocyte-specific calcium-binding S100 proteins as clinical laboratory markers of inflammation; Clinica Chimica Acta, 2004, pp. 37-51.

Gomes et al., The Apoptotic, angiogenic and Cell Proliferation Genes CD63, S100A6 e GNB2L1 are Altered in Patients with Endometriosis; 2018, 8-pages.

Hsu et al., Invasive and non-invasive methods for the diagnosis of endometriosis; Clin Obstet Gynecol., 2010, vol. 53, No. 2, pp. 413-419.

Irungu et al., Discovery of non-invasive biomarkers for the diagnosis of endometriosis; Clinical Proteomics; 2019, vol. 16, No. 14, 16-pages.

Jurewicz et al., Tubulin-dependent secretion of S100A6 and cellular signaling pathways activated by S100A;6-integrin Beta1 interaction; Cellular Signalling, 2018, vol. 42, pp. 21-29.

Kennedy et al., ESHRE guideline for the diagnosis and treatment of endometriosis; Human Reproduction, 2005, vol. 20, No. 10, pp. 2696-2704.

Morotti et al., Peripheral changes in endometriosis-associated pain; Human Reproduction Update, 2014, vol. 20, No. 5, pp. 717-736.

Tokushige et al., Nerve fibres in peritoneal endometriosis; Human Reproduction; 2006, vol. 21, No. 11, pp. 3001-3007.

NICE, National Institute for Health and Care Excellence; Endometriosis: diagnosis and management; NICE Guideline, 2017, 24-pages.

Nisenblat et al., Cochrane Library; Blood biomarkers for the non-invasive diagnosis of endometriosis (Review); 581-pages.

Otsuka et al., Physiological Reviews; 1993, vol. 73, No. 2., 80-pages.

Parasar et al., Endometriosis: Epidemiology, Diagnosis and Clinical Management; Curr Obstet Gynecol Rep., 2017, vol. 6, No. 1, pp. 34-41.

Peng et al., Upregulation of S100A6 in patients with endometriosis and its role in ectopic endometrial stromal cells; Gynecological Endocrinology; 7-pages, 2017 p. 815-820.

Rose et al., Early Non-Invasive Diagnosis of Endometriosis in Infertile Women using Biomarkers Found in Cervico-Vaginal Fluid, 2009, 2-pages.

Sinaii et al., Differences in characteristics among 1,000 woen with endometriosis based on extent of disease; Fertil Steril, 2008, vol. 89, No. 3, pp. 538-545.

Symons et al., The immunopathophysiology of Endometriosis; Trends in Molecular Medicine; CellPress reviews., 2018, vol. 24, No. 9, 15-pages.

Wang et al., Hyperinnervationin Intestinal Deep INflitrating Endometriosis; The Journal of Minimally Invasive Gynecology; 2009, vol. 16, No. 6, 7-pages.

Wang et al., Rich innervation of deep infiltrating endometriosis; Human Reproduction, 2009, vol. 24, No. 4, pp. 827-834.

Xiang et al., Transcriptome sequencing of adenomyosis eutopic endometrium: A new insight into its pathophysiology; J. Cell Mol Med., 2019, 11-pages.

Yan et al., Neuropeptides Substance P and Calcitonin Gene Related Peptide Accelerate the Development and Fibrogenesis of Endometriosis; Scientific Reports; 2019, 22-pages.

Zhang et al., Effect of S100A6 gene silencing on the biological features of eutopic endometrial stromal cells and beta-catenin expression; Molecular Medicine Reports, 2017, vol. 15, pp. 1279-1285.

* cited by examiner

S100A8 + Dysmenorrhea

AUC: 0.8625

Mean values

Controls (n= 10): 85500.0 pg/mL
Cases stages 1-4 (n= 15): 162940.0 pg/mL

Median values

Controls (n= 10): 65950.0 pg/mL

Cases stages 1-4 (n= 15): 136000.0 pg/mL

Mean values

Controls (n= 10): 66640.0 pg/mL

Cases stages 1/2 (n= 8): 115950.0 pg/mL
Cases stages 3/4 (n= 7): 132200.0 pg/mL

Median values

Controls (n= 10): 65250.0 pg/mL

Cases stages 1/2 (n= 8): 101200.0 pg/mL
Cases stages 3/4 (n= 7): 127000.0 pg/mL

S100A8 AS BLOOD BIOMARKER FOR THE NON-INVASIVE DIAGNOSIS OF ENDOMETRIOSIS

CROSS-REFERENCE TO RELATED APPLICATIONS

This application is a continuation of International Application No. PCT/EP2020/070427 filed Jul. 20, 2020, which claims priority to European Application 19187474.2 filed Jul. 22, 2019, the disclosures of which are hereby incorporated by reference in their entirety.

The present invention relates to methods of assessing whether a patient has endometriosis or is at risk of developing endometriosis, to methods of selecting a patient for therapy, and methods of monitoring a patient suffering from endometriosis or being treated for endometriosis, by determining the amount or concentration of S100A8 in a sample of the patient, and comparing the determined amount or concentration to a reference.

BACKGROUND OF THE INVENTION

Endometriosis is defined as the presence of endometrial glands and stroma-like lesions outside of the uterus. The lesions can be peritoneal lesions, superficial implants or cysts on the ovary, or deep infiltrating disease. Endometriosis affects 5-8% of all women of reproductive age and 70% of women with chronic pelvic pain. The prevalence of endometriosis has been estimated at 176 million women worldwide (Adamson et al. J Endometr. 2010; 2: 3-6). For many of these women there is often a delay in diagnosis of endometriosis resulting in unnecessary suffering and reduced quality of life. In patients aged 18-45 years, there is delay of 7-10 years. As most women with endometriosis report the onset of symptoms during adolescence, early referral, diagnosis, identification of disease and treatment may mitigate pain preventing disease progression. Barriers to early diagnosis include the high cost of diagnosis and treatment in adolescent patients and presentation of confounding symptoms such as cyclic and non-cyclic pain (Parasar et al. Curr Obstet Gynecol Rep. 2017; 6: 34-41).

Gold standard for the diagnosis of endometriosis is laparoscopic visualization and subsequent histological confirmation. Until now, there are no non-invasive methods for the diagnosis of endometriosis (Hsu et al. Clin Obstet Gynecol 2010: 53: 413-419). During a diagnostic laparoscopy, a gynaecologist with training and skills in laparoscopic surgery for endometriosis should perform a systematic inspection of the pelvis (NICE guideline NG73, 2017). Surgical visualization requires good expertise, training and skills for reliable diagnosis. The fact that laparoscopic surgery is needed for diagnosis, which is avoided by doctors as long as possible, leads to a delay in the diagnosis for 7-10 years. The lack of a non-invasive diagnostic test significantly contributes to the long delay between onset of the symptoms and definitive diagnosis of endometriosis (Signorile and Baldi. J Cell Physiol 2014; 229: 1731-1735). Thus there is an unmet medical need for a non-invasive test for the diagnosis of endometriosis, in particular for the diagnosis of early, minimal and mild endometriosis (revised American Society for Reproductive Medicine rASRM stages I-II).

Adenomyosis is defined as infiltration of benign endometrial glands and stroma into the myometrium, the outer muscle layer of the uterus. There are 3 distinct adenomyosis sybtypes, depending on the morphology and location: internal adenomyosis, external adenomyosis and adenomyomas.

Internal adenomyosis can be further classified into focal, diffuse and superficial adenomyosis (Bazot M et al. Fertil Steril. 2018; 109:389-397). Adenomyosis can also be classified based on Magnetic Resonance Imaging (MRI) findings, according to whether it is located in the outer or the inner uterine layer, into 4 subtypes I-IV. Common signs and symptoms of adenomyosis include heavy bleeding during menstruation (menorrhagia) and in-between menstrual periods (metrorrhagia), dysmenorrhea, chronic pelvic pain, dyspareunia and infertility (Chapron C et al. Hum Reprod Update. 2020; 26:392-411).

Transvaginal ultrasound (TVUS) and Magnetic Resonance Imaging (MRI) are currently used to diagnose adenomyosis, with an overall sensitivity/specificity of 83.8%, 63.9% and 77.3%, 89.8% respectively. Among the different adenomyosis types, diffuse adenomyosis is more difficult to detect by imaging and requires an experienced sonographer. Also, access to imaging equipment is limited, especially among primary care healthcare professionals, and requires trained staff and specialized resources. Therefore, a non-invasive blood-based test would allow medical assessment of adenomyosis without a need for imaging device, reduce the inter-operator variability and enable a more standardized diagnosis of the condition (Chapron C et al. Hum Reprod Update. 2020; 26:392-411).

Non-invasive diagnosis of endometriosis would allow earlier diagnosis and treatment, with the potential to improve quality of life and reduce the societal costs related to endometriosis, and has therefore been selected as a research priority by the World Endometriosis Society (WES) and the World Endometriosis Research Foundation (WERF) (Fassbender et al., Springer, Peripheral Blood Biomarkers for Endometriosis. 2017). Thus, a non-invasive tool to diagnose endometriosis could facilitate earlier diagnosis and intervention that could ultimately improve quality of life and preserve fertility (Parasar et al. Curr Obstet Gynecol Rep. 2017; 6: 34-41).

Blood biomarkers are essential to reduce the time delay of diagnosing endometriosis that require laparoscopy. To date no non-invasive biomarker for diagnosis of endometriosis was identified. CA-125 is one of the most commonly used blood biomarkers, however, it's diagnostic utility is limited to endometriosis rASRM stages III and IV (Nisenblat et al., Cochrane Database of Systematic Reviews. 2016; 5: CD012179).

Increased S100A8 levels have been reported in chronic inflammatory conditions (psoriasis, rheumatoid arthritis, cystic fibrosis, inflammatory bowel disease, Crohn's disease, systemic lupus erythematosus, progressive systemic sclerosis) and several types of malignancies (Foell D. et al. *Clin Chim Acta* 2004; 344:37-51). Tissue microarray analysis of messenger RNA (mRNA) revealed S100A8 in the list of genes that showed the highest upregulation in endometriotic lesions when compared to endometrium from women without endometriosis (Burney R. et al. Endocrinol. 2007; 148(8):2814-2826). At the tissue level, S100A8 mRNA was shown to be upregulated by 9.5-fold within ectopic lesions when compared to eutopic endometrium from patients diagnosed with endometriosis, as shown by tissue microarray analysis (Eyster K. et al. Fertil Steril. 2007; 88: 1505-33). Proteomic analysis using liquid chromatography—Tandem Mass Spectrometry in peritoneal fluid isolated from women diagnosed with endometriosis by invasive laparoscopy revealed higher S100A8 levels in patients with moderate-severe endometriosis (rASRM stages III-IV) compared to those diagnosed with minimal-mild disease (rASRM stages I-II) (Ferrero et al. Gynecol Endocrinol. 2009; 24(8):433-441).

SUMMARY OF THE INVENTION

In a first aspect, the present invention relates to a method of assessing whether a patient has endometriosis or is at risk of developing endometriosis, comprising determining the amount or concentration of S100A8 in a sample of the patient, and comparing the determined amount or concentration to a reference.

In a second aspect, the present invention relates to a method of selecting a patient for therapy [in particular drug-based therapy or surgical therapy (laparoscopy)] of endometriosis, comprising determining the amount or concentration of S100A8 in a sample of the patient, and comparing the determined amount or concentration to a reference.

In a third aspect, the present invention relates to a method of monitoring a patient suffering from endometriosis or being treated for endometriosis, comprising determining the amount or concentration of S100A8 in a sample of the patient, and comparing the determined amount or concentration to a reference.

LIST OF FIGURES

FIGS. 1A-1C: Receiver Operator Curve (ROC) analyses for single biomarkers (FIG. 1A) S100A8, (FIG. 1B) CA-125 and (FIG. 1C) clinical symptom dysmenorrhea.

x-axis=specificity, y-axis=sensitivity

Figure 2:
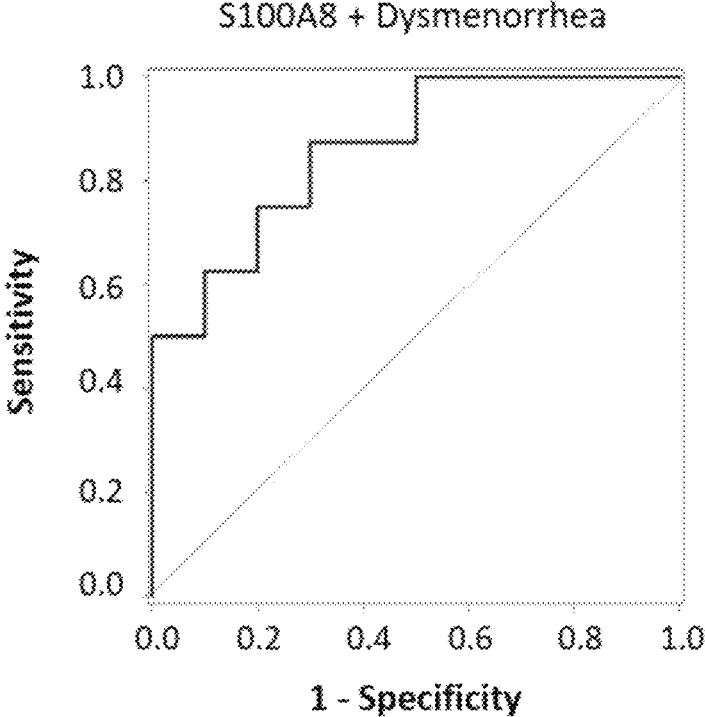

FIG. 2: Receiver Operator Curve (ROC) analyses for combination of S100A8 and clinical symptoms.

x-axis=specificity, y-axis=sensitivity

Figure 3A:
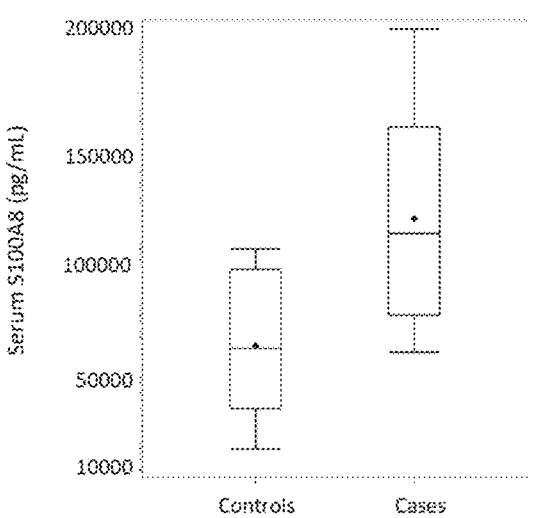
Figure 3B:
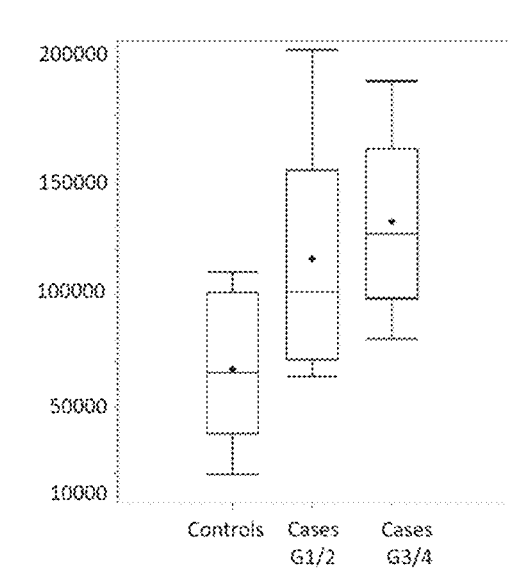

FIGS. 3A & 3B: Box plots of S100A8 in endometriosis cases and controls (FIG. 3A) and S100A8 in cases rASRM stage I-II (G1/2), rASRM stages III-IV (G3/4) and Controls (FIG. 3B).

Figures 4A, 4B:
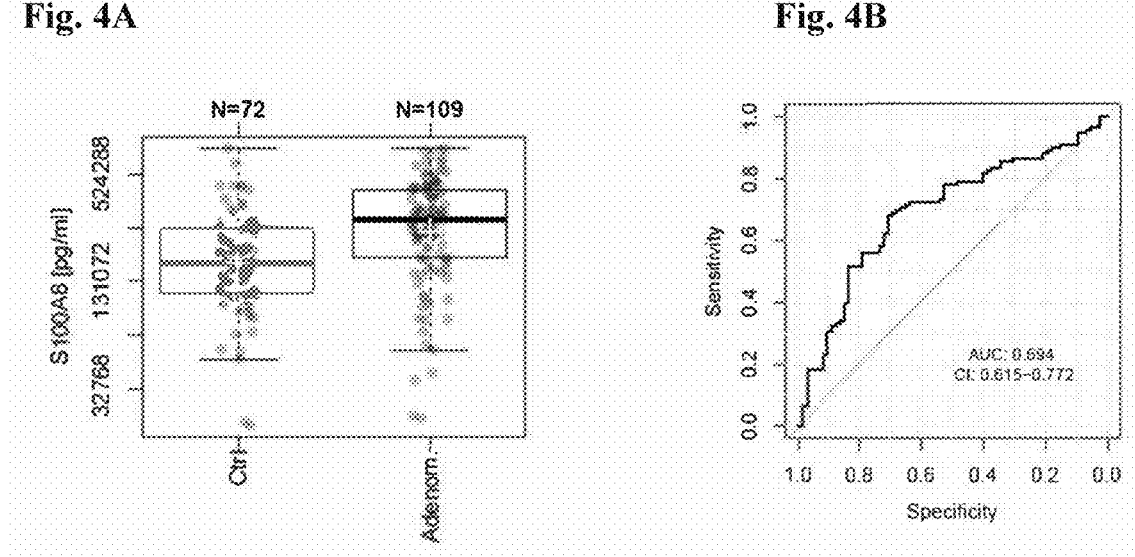

FIGS. 4A & 4B: Box plots and ROC curves of serum levels of S100A8 in adenomyosis cases and controls.

Figures 5A, 5B:
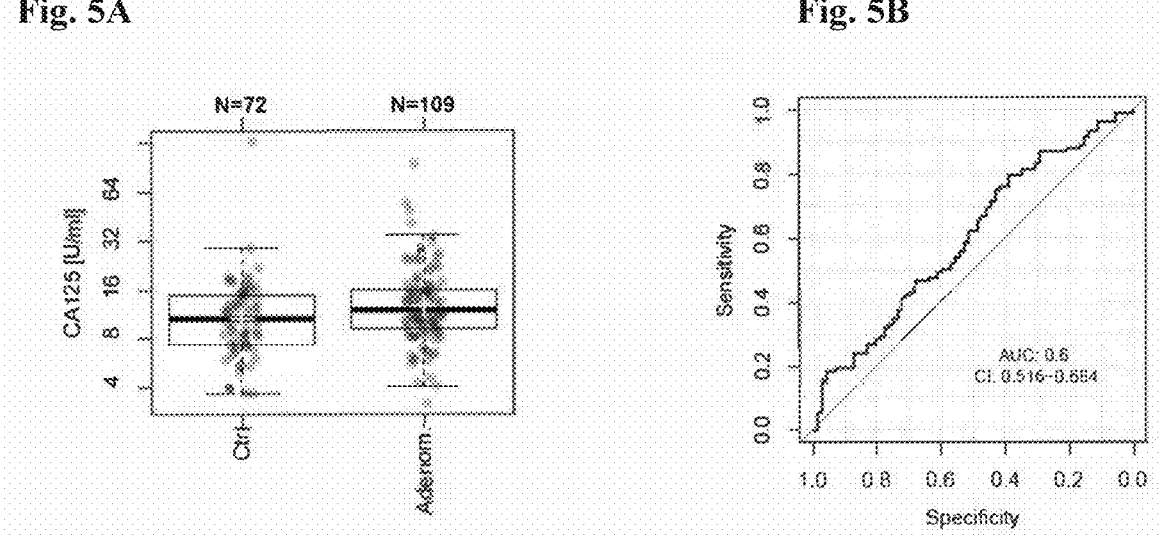

FIGS. 5A & 5B: Box plots and ROC curves of serum levels of CA-125 in adenomyosis cases and controls.

LIST OF TABLES

Table 1: Diagnostic performance of biomarker S100A8 and biomarker combinations in women with endometriosis and controls.

Table 2: Cut-off for combination of various biomarkers to predict endometriosis based on multivariable logistic regression analysis and Youden's index.

Table 3: Diagnostic performance of single biomarkers S100A8 and CA-125 in adenomyosis cases and controls.

DETAILED DESCRIPTION OF THE INVENTION

We show for the first time that S100A8 measured in blood is increased in women with endometriosis compared to controls. S100A8 levels are already increased in endometriosis stages I and II (minimal/mild endometriosis). We also demonstrate that combining S100A8 with dysmenorrhea (menstrual cycle-dependent pain) increased the diagnostic performance for distinguishing women with endometriosis from those without endometriosis. There is an unmet medical need for a non-invasive test for the reliable diagnosis of endometriosis, and in particular early endometriosis. S100A8 alone or in combination with dysmenorrhea/lower abdominal pain and/or CA-125 has the advantage of a non-invasive blood based test that identifies women with early endometriosis, in particular peritoneal endometriosis (rASRM stages I-II) that is currently not possible with a non-invasive test.

Definitions

The word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "150 mg to 600 mg" should be interpreted to include not only the explicitly recited values of 150 mg to 600 mg, but to also include individual values and sub-ranges within the indicated range. Thus, included in this numerical range are individual values such as 150, 160, 170, 180, 190, . . . 580, 590, 600 mg and sub-ranges such as from 150 to 200, 150 to 250, 250 to 300, 350 to 600, etc. This same principle applies to ranges reciting only one numerical value. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "indicator" as used herein, refers to a sign or signal for a condition or is used to monitor a condition. Such a "condition" refers to the biological status of a cell, tissue or organ or to the health and/or disease status of an individual. An indicator may be the presence or absence of a molecule, including but not limited to peptide, protein, and nucleic acid, or may be a change in the expression level or pattern of such molecule in a cell, or tissue, organ or individual. An indicator may be a sign for the onset, development or presence of a disease in an individual or for the further progression of such disease. An indicator may also be a sign for the risk of developing a disease in an individual.

In the context of present invention, the term "biomarker" refers to a substance within a biological system that is used as an indicator of a biological state of said system. In the art, the term "biomarker" is sometimes also applied to means for the detection of said endogenous substances (e.g. antibodies, nucleic acid probes etc, imaging systems). In the context of present invention, the term "biomarker" shall be only applied for the substance, not for the detection means. Thus, biomarkers can be any kind of molecule present in a living organism, such as a nucleic acid (DNA, mRNA, miRNA, rRNA etc.), a protein (cell surface receptor, cytosolic protein etc.), a metabolite or hormone (blood sugar, insulin, estrogen, etc.), a molecule characteristic of a certain modification of another molecule (e.g. sugar moieties or phosphoryl residues on proteins, methyl-residues on genomic DNA) or a substance that has been internalized by the organism or a metabolite of such a substance.

"S100A8", S100 calcium binding protein A8 (calgranulin-A; myeloid-related protein 8, MRP8) is a 10.8 kilodalton calcium- and zinc-binding protein and belongs to the S100 protein family. S100 family makes up the largest subgroup of the Ca2+-binding EF-hand (helix E-loop-helix F) proteins. S100 proteins are soluble in a 100%-saturated solution with ammonium sulphate at neutral pH, where their name comes from. S100A8 is predominantly expressed in monocytes, neutrophils and dendritic cells but also in various other activated cell types, such as fibroblasts, mature macrophages, vascular endothelial cells and keratinocytes (Ingersoll et al. Blood. 2010; 115(3): e10-9). S100A8 is a DAMP (Damage-Associated Molecular Pattern) molecule, released from damaged or stressed cells and further acts as endogenous danger signal to activate inflammatory response, through binding to TLR4 (Toll-Like Receptor 4) and RAGE (Receptor for Advanced Glycosylation End products) receptors. At the site of inflammation, S100A8 acts as a chemotactic factor by inducing neutrophil adhesion and macrophage activation (Schmidt et al. Semin Thromb Hemost. 2000; 26(5):285-293).

"CA-125", the Carbohydrate antigen 125, sometimes named as Cancer Antigen 125 or Tumor Antigen 125, is a mucin-type glycoprotein, produced by the MUC16 gene, and associated with the cellular membrane. CA-125 is a biomarker for epithelial cell ovarian cancer being derived from coelomic epithelia including the endometrium, fallopian tube, ovary, and peritoneum. Diagnostic use of CA-125 is limited to endometriosis stages III and IV (moderate and severe endometriosis) with moderate sensitivity.

"Symptoms" of a disease are implication of the disease noticeable by the tissue, organ or organism having such disease and include but are not limited to pain, weakness, tenderness, strain, stiffness, and spasm of the tissue, an organ or an individual. "Signs" or "signals" of a disease include but are not limited to the change or alteration such as the presence, absence, increase or elevation, decrease or decline, of specific indicators such as biomarkers or molecular markers, or the development, presence, or worsening of symptoms. Symptoms of pain include, but are not limited to an unpleasant sensation that may be felt as a persistent or varying burning, throbbing, itching or stinging ache.

The term "disease" and "disorder" are used interchangeably herein, referring to an abnormal condition, especially an abnormal medical condition such as an illness or injury, wherein a tissue, an organ or an individual is not able to efficiently fulfil its function anymore. Typically, but not necessarily, a disease is associated with specific symptoms or signs indicating the presence of such disease. The presence of such symptoms or signs may thus, be indicative for a tissue, an organ or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a tissue, organ or organism to fulfil its function efficiently, whereas the "bettering" of a disease is typically characterised by an increase in the ability of a tissue, an organ or an individual to fulfil its function efficiently. A tissue, an organ or an individual being at "risk of developing" a disease is in a healthy state but shows potential of a disease emerging. Typically, the risk of developing a disease is associated with early or weak signs or symptoms of such disease. In such case, the onset of the disease may still be prevented by treatment.

Examples of a disease include but are not limited to inflammatory diseases, infectious diseases, cutaneous conditions, endocrine diseases, intestinal diseases, neurological disorders, joint diseases, genetic disorders, autoimmune diseases, traumatic diseases, and various types of cancer.

"Endometriosis" is a chronic, hormone-dependent, inflammatory disease that is characterized by lesions of endometrial-like tissue outside of the uterus. Clinical presentation of endometriosis varies significantly from patient to patient. Endometriosis patients often present with symptoms such as intermenstrual bleeding, painful periods (dysmenorrhea), painful intercourse (dyspareunia), painful defecation (dyschezia) and painful urination (dysuria). Pelvic pain due to endometriosis is usually chronic (lasting ≥6 months) and is associated with dysmenorrhea (in 50 to 90% of cases), dyspareunia, deep pelvic pain, and lower abdominal pain with or without back and loin pain. The pain can occur unpredictably and intermittently throughout the menstrual cycle or it can be continuous, and it can be dull, throbbing, or sharp, and exacerbated by physical activity. Bladder- and bowel-associated symptoms (nausea, distention, and early satiety) are typically cyclic. Pain often worsens over time and may change in character; infrequently, women report burning or hypersensitivity, symptoms that are suggestive of a neuropathic component. Often, endometriosis can be asymptomatic, only coming to a clinician's attention during evaluation for infertility (Sinaii et al. Fertil Steril. 2008; 89(3): 538-545). In women with endometriosis, there is a reduced monthly fecundity rate (2-10%) compared with fertile couples (15-20%). Although endometriosis impairs fertility, it does not usually completely prevent conception (Fadhlaoui et al. Front Surg. 2014; 1: 24).

The most commonly affected sites of endometriosis are the pelvic organs and peritoneum, although other parts of the body such as the lungs are occasionally affected. The extent of the disease varies from a few, small lesions on otherwise normal pelvic organs to large, ovarian endometriotic cysts (endometriomas) and/or extensive fibrosis and adhesion formation causing marked distortion of pelvic anatomy. Based on the location, endometriotic lesions can be classified into peritoneal endometriosis, ovarian endometriotic cysts (endometrioma), deep nodules (deep infiltrating endometriosis), and adenomyosis (Kennedy et al. Hum Reprod. 2005; 20(10): 2698-2704).

The term "rASRM stage" or "rASRM staging" refers to the revised classification system established by the American Society for Reproductive Medicine (ASRM) describing the severity of endometriosis based on the findings at surgery (laparoscopy). The classification is based on the morphology of peritoneal and pelvic implants such as red, white and black lesions, percentage of involvement of each lesion should be included. Number, size, and location endometrial implants, plaques, endometriomas and adhesions should be noted. Endometriosis in bowel, urinary tract, fallopian tube, vagina, cervix, skin, or other locations should be documented per ASRM guidelines. Stages of endometriosis according to ASRM guidelines are stage I, II, III, and IV determined based on the point scores and correspond to minimal, mild, moderate and severe endometriosis. The rASRM stages I & II endometriosis (minimal to mild endometriosis) are defined by superficial peritoneal endometriosis, possible presence of small deep lesions, absence of endometrioma and/or mild filmy adhesion. The rASRM stages III and IV endometriosis (moderate to severe endometriosis) are defined by the presence of superficial peritoneal endometriosis, deep infiltrating endometriosis with moderate to extensive adhesions between the uterus and bowels and/or endometrioma cysts with moderate to extensive adhesions involving the ovaries and tubes.

The term "VAS", the Visual Analog Scale, is an instruments to assess the intensity of pain. The VAS consists of a 10-cm long horizontal line with its extremes marked as 'no pain' and 'worst pain imaginable'. Each patient ticks her pain level on the line and the distance from 'no pain' on the extreme left to the tick mark is measured in centimeters, yielding a pain score from 0 to 10. 'No pain' corresponds to a pain score of 0, 'worst pain imaginable' corresponds to a pain score of 10. In women with endometriosis dysmenorrhea is associated with the highest perception of pain with a mean VAS score of about 6 (Cozzolino et al. Rev Bras Ginecol Obstet. 2019; 41(3): 170-175).

As used herein, a "patient" means any mammal, fish, reptile or bird that may benefit from the diagnosis, prognosis or treatment described herein. In particular, a "patient" is selected from the group consisting of laboratory animals (e.g. mouse, rat, rabbit, or zebrafish), domestic animals (including e.g. guinea pig, rabbit, horse, donkey, cow, sheep, goat, pig, chicken, camel, cat, dog, turtle, tortoise, snake, lizard or goldfish), or primates including chimpanzees, bonobos, gorillas and human beings. It is particularly preferred that the "patient" is a human being.

The term "sample" or "sample of interest" are used interchangeably herein, referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, urine, saliva, and lymphatic fluid, or solid samples such as tissue extracts, cartilage, bone, synovium, and connective tissue. Analysis of a sample may be accomplished on a visual or chemical basis. Visual analysis includes but is not limited to microscopic imaging or radiographic scanning of a tissue, organ or individual allowing for morphological evaluation of a sample. Chemical analysis includes but is not limited to the detection of the presence or absence of specific indicators or alterations in their amount, concentration or level. The sample is an in vitro sample, it will be analyzed in vitro and not transferred back into the body.

The term "amount" as used herein encompasses the absolute amount of a biomarker as referred to herein, the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts measured from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the amount of the biomarker in the sample from the subject with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer-assisted. Thus, the comparison may be carried out by a computing device. The value of the measured or detected amount of the biomarker in the sample from the subject and the reference amount can be, e.g., compared to each other and the said comparison can be automatically carried out by a computer program executing an algorithm for the comparison. The computer program carrying out the said evaluation will provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provides the desired assessment in a suitable output format.

The expression "comparing the amount or concentration determined to a reference" is merely used to further illustrate what is obvious to the skilled artisan anyway. A reference concentration is established in a control sample The term "reference sample" or "control sample" as used herein, refers to a sample which is analysed in a substantially identical manner as the sample of interest and whose information is compared to that of the sample of interest. A reference sample thereby provides a standard allowing for the evaluation of the information obtained from the sample of interest. A control sample may be derived from a healthy or normal tissue, organ or individual, thereby providing a standard of a healthy status of a tissue, organ or individual. Differences between the status of the normal reference sample and the status of the sample of interest may be indicative of the risk of disease development or the presence or further progression of such disease or disorder. A control sample may be derived from an abnormal or diseased tissue, organ or individual thereby providing a standard of a diseased status of a tissue, organ or individual. Differences between the status of the abnormal reference sample and the status of the sample of interest may be indicative of a lowered risk of disease development or the absence or bettering of such disease or disorder. A reference sample may also be derived from the same tissue, organ, or individual as the sample of interest but has been taken at an earlier time point. Differences between the status of the earlier taken reference sample and the status of the sample of interest may be indicative of the progression of the disease, i.e. a bettering or worsening of the disease over time.

The control sample may be an internal or an external control sample. An internal control sample is used, i.e. the marker level(s) is(are) assessed in the test sample as well as in one or more other sample(s) taken from the same subject to determine if there are any changes in the level(s) of said marker(s). For an external control sample the presence or amount of a marker in a sample derived from the individual is compared to its presence or amount in an individual known to suffer from, or known to be at risk of, a given condition; or an individual known to be free of a given condition, i.e., "normal individual".

It will be appreciated by the skilled artisan that such external control sample may obtained from a single individual or may be obtained from a reference population that is age-matched and free of confounding diseases. Typically, samples from 100 well-characterized individuals from the appropriate reference population are used to establish a "reference value". However, reference population may also be chosen to consist of 20, 30, 50, 200, 500 or 1000 individuals. Healthy individuals represent a preferred reference population for establishing a control value.

For example, a marker concentration in a patient sample can be compared to a concentration known to be associated with a specific course of a certain disease. Usually the sample's marker concentration is directly or indirectly correlated with a diagnosis and the marker concentration is e.g. used to determine whether an individual is at risk for a certain disease. Alternatively, the sample's marker concentration can e.g. be compared to a marker concentration known to be associated with a response to therapy in a certain disease, the diagnosis of a certain disease, the assessment of the severity of a certain disease, the guidance for selecting an appropriate drug to a certain disease, in judging the risk of disease progression, or in the follow-up of patients. Depending on the intended diagnostic use an appropriate control sample is chosen and a control or reference value for the marker established therein. As also clear to the skilled artisan, the absolute marker values established in a control sample will be dependent on the assay used.

The terms "lowered" or "decreased" level of an indicator refer to the level of such indicator in the sample being reduced in comparison to the reference or reference sample.

The terms "elevated" or "increased" level of an indicator refer to the level of such indicator in the sample being higher in comparison to the reference or reference sample. E.g. a protein that is detectable in higher amounts in a fluid sample of one individual suffering from a given disease than in the same fluid sample of individuals not suffering from said disease, has an elevated level.

The term "measurement", "measuring" or "determining" preferably comprises a qualitative, a semi-quantitative or a quantitative measurement.

The term "immunoglobulin (Ig)" as used herein refers to immunity conferring glycoproteins of the immunoglobulin superfamily. "Surface immunoglobulins" are attached to the membrane of effector cells by their transmembrane region and encompass molecules such as but not limited to B-cell receptors, T-cell receptors, class I and II major histocompatibility complex (MHC) proteins, beta-2 microglobulin (~2M), CD3, CD4 and CDS.

Typically, the term "antibody" as used herein refers to secreted immunoglobulins which lack the transmembrane region and can thus, be released into the bloodstream and body cavities. Human antibodies are grouped into different isotypes based on the heavy chain they possess. There are five types of human Ig heavy chains denoted by the Greek letters: α, γ, δ, ε, and μ. The type of heavy chain present defines the class of antibody, i.e. these chains are found in IgA, IgD, IgE, IgG, and IgM antibodies, respectively, each performing different roles, and directing the appropriate immune response against different types of antigens. Distinct heavy chains differ in size and composition; and may comprise approximately 450 amino acids (Janeway et al. (2001) Immunobiology, Garland Science). IgA is found in mucosal areas, such as the gut, respiratory tract and urogenital tract, as well as in saliva, tears, and breast milk and prevents colonization by pathogens (Underdown & Schiff (1986) Annu. Rev. Immunol. 4:389-417). IgD mainly functions as an antigen receptor on B cells that have not been exposed to antigens and is involved in activating basophils and mast cells to produce antimicrobial factors (Geisberger et al. (2006) Immunology 118:429-437; Chen et al. (2009) Nat. Immunol. 10:889-898). IgE is involved in allergic reactions via its binding to allergens triggering the release of histamine from mast cells and basophils. IgE is also involved in protecting against parasitic worms (Pier et al. (2004) Immunology, Infection, and Immunity, ASM Press). IgG provides the majority of antibody-based immunity against invading pathogens and is the only antibody isotype capable of crossing the placenta to give passive immunity to fetus (Pier et al. (2004) Immunology, Infection, and Immunity, ASM Press). In humans there are four different IgG subclasses (IgG1, 2, 3, and 4), named in order of their abundance in serum with IgG1 being the most abundant (~66%), followed by IgG2 (~23%), IgG3 (~7%) and IgG (~4%). The biological profile of the different IgG classes is determined by the structure of the respective hinge region. IgM is expressed on the surface of B cells in a monomeric form and in a secreted pentameric form with very high avidity. IgM is involved in eliminating pathogens in the early stages of B cell mediated (humoral) immunity before sufficient IgG is produced (Geisberger et al. (2006) Immunology 118:429-437). Antibodies are not only found as monomers but are also known to form dimers of two Ig units (e.g. IgA), tetramers of four Ig units (e.g. IgM of teleost fish), or pentamers of five Ig units (e.g. mammalian IgM). Antibodies are typically made of four polypeptide chains comprising two identical heavy chains and identical two light chains which are connected via disulfide bonds and resemble a "Y"-shaped macro-molecule. Each of the chains comprises a number of immunoglobulin domains out of which some are constant domains and others are variable domains. Immunoglobulin domains consist of a 2-layer sandwich of between 7 and 9 antiparallel ~-strands arranged in two ~-sheets. Typically, the heavy chain of an antibody comprises four Ig domains with three of them being constant (CH domains: CHI. CH2. CH3) domains and one of the being a variable domain (V H). The light chain typically comprises one constant Ig domain (CL) and one variable Ig domain (V L). Exemplified, the human IgG heavy chain is composed of four Ig domains linked from N- to C-terminus in the order VwCH1-CH2-CH3 (also referred to as VwCyl-Cy2-Cy3), whereas the human IgG light chain is composed of two immunoglobulin domains linked from N- to C-terminus in the order VL-CL, being either of the kappa or lambda type (VK-CK or VA.-CA.). Exemplified, the constant chain of human IgG comprises 447 amino acids. Throughout the present specification and claims, the numbering of the amino acid positions in an immunoglobulin are that of the "EU index" as in Kabat, E. A., Wu, T. T., Perry, H. M., Gottesman, K. S., and Foeller, C., (1991) Sequences of proteins of immunological interest, 5[th]ed. U.S. Department of Health and Human Service, National Institutes of Health, Bethesda, MD. The "EU index as in Kabat" refers to the residue numbering of the human IgG lEU antibody. Accordingly, CH domains in the context of IgG are as follows: "CHI" refers to amino acid positions 118-220 according to the EU index as in Kabat; "CH2" refers to amino acid positions 237-340 according to the EU index as in Kabat; and "CH3" refers to amino acid positions 341-44 7 according to the EU index as in Kabat.

The terms "full-length antibody", "intact antibody", and "whole antibody" are used herein interchangeably to refer to an antibody in its substantially intact form, not antibody fragments as defined below. The terms particularly refer to an antibody with heavy chains that contain an Fc region.

Papain digestion of antibodies produces two identical antigen binding fragments, called "Fab fragments" (also referred to as "Fab portion" or "Fab region") each with a single antigen binding site, and a residual "Fe fragment" (also referred to as "Fe portion" or "Fe region") whose name reflects its ability to crystallize readily. The crystal structure of the human IgG Fe region has been determined (Deisen-hofer (1981) Biochemistry 20:2361-2370). In IgG, IgA and IgD isotypes, the Fe region is composed of two identical protein fragments, derived from the CH2 and CH3 domains of the antibody's two heavy chains; in IgM and IgE isotypes, the Fe regions contain three heavy chain constant domains (CH2-4) in each polypeptide chain. In addition, smaller immunoglobulin molecules exist naturally or have been constructed artificially. The term "Fab' fragment" refers to a Fab fragment additionally comprise the hinge region of an Ig molecule whilst "F(ab)2 fragments" are understood to comprise two Fab' fragments being either chemically linked or connected via a disulfide bond. Whilst "single domain antibodies (sdAb)" (Desmyter et al. (1996) Nat. Structure Biol. 3:803-811) and "Nanobodies" only comprise a single VH domain, "single chain Fv (scFv)" fragments comprise the heavy chain variable domain joined via a short linker peptide to the light chain variable domain (Huston et al. (1988) Proc. Natl. Acad. Sci. USA 85, 5879-5883). Divalent single-chain variable fragments (di-scFvs) can be engi-neered by linking two scFvs (scFvA-scFvB). This can be done by producing a single peptide chain with two VH and two VL regions, yielding "tandem scFvs" (VHA-VLA-VHB-VLB). Another possibility is the creation of scFvs with linkers that are too short for the two variable regions to fold together, forcing scFvs to dimerize. Usually linkers with a length of 5 residues are used to generate these dimers. This type is known as "diabodies". Still shorter linkers (one or two amino acids) between a V H and V L domain lead to the formation of monospecific trimers, so-called "triabodies" or "tribadies". Bispecific diabodies are formed by expressing to chains with the arrangement VHA-VLB and VHB-VLA or VLA-VHB and VLB-VHA, respectively. Singlechain dia-bodies (scDb) comprise a VHA-VLB and a VHB-VLA fragment which are linked by a linker peptide (P) of 12-20 amino acids, preferably 14 amino acids, (VHA-VLB-P-VHB-VLA). "Bi-specific T-cell engagers (BiTEs)" are fusion proteins consisting of two scFvs of different antibod-ies wherein one of the scFvs binds to T cells via the CD3 receptor, and the other to a tumor cell via a tumor specific molecule (Kufer et al. (2004) Trends Biotechnol. 22:238-244). Dual affinity retargeting molecules ("DART" mol-ecules) are diabodies additionally stabilized through a C-ter-minal disulfide bridge.

Accordingly, the term "antibody fragments" refers to a portion of an intact antibody, preferably comprising the antigen-binding region thereof. Antibody fragments include but are not limited to Fab, Fab', F(ab')$_2$, Fv fragments; diabodies; sdAb, nanobodies, scFv, di-scFvs, tandem scFvs, triabodies, diabodies, scDb, BiTEs, and DARTs.

The term "binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including but not limited to surface plasmon resonance based assay (such as the BIAcore assay as described in PCT Application Publication No. WO2005/012359); enzyme-linked immunoabsorbent assay (ELISA); and competition assays (e.g. RIA's). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Sandwich immunoassays" are broadly used in the detec-tion of an analyte of interest. In such assay the analyte is "sandwiched" in between a first antibody and a second antibody. Typically, a sandwich assay requires that capture and detection antibody bind to different, non-overlapping epitopes on an analyte of interest. By appropriate means such sandwich complex is measured and the analyte thereby quantified. In a typical sandwich-type assay, a first antibody bound to the solid phase or capable of binding thereto and a detectably-labeled second antibody each bind to the ana-lyte at different and non-overlapping epitopes. The first analyte-specific binding agent (e.g. an antibody) is either covalently or passively bound to a solid surface. The solid surface is typically glass or a polymer, the most commonly used polymers being cellulose, polyacrylamide, nylon, poly-styrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 37° C. inclusive) to allow for binding between the first or capture antibody and the corresponding antigen. Following the incubation period, the solid phase, comprising the first or capture antibody and bound thereto the antigen can be washed, and incubated with a secondary or labeled antibody binding to another epitope on the antigen. The second antibody is linked to a reporter mol-ecule which is used to indicate the binding of the second antibody to the complex of first antibody and the antigen of interest.

An extremely versatile alternative sandwich assay format includes the use of a solid phase coated with the first partner of a binding pair, e.g. paramagnetic streptavidin-coated microparticles. Such microparticles are mixed and incubated with an analyte-specific binding agent bound to the second partner of the binding pair (e.g. a biotinylated antibody), a sample suspected of comprising or comprising the analyte, wherein said second partner of the binding pair is bound to said analyte-specific binding agent, and a second analyte-specific binding agent which is detectably labeled. As obvi-ous to the skilled person these components are incubated under appropriate conditions and for a period of time sufficient for binding the labeled antibody via the analyte, the analyte-specific binding agent (bound to) the second partner of the binding pair and the first partner of the binding pair to the solid phase microparticles. As appropriate such assay may include one or more washing step(s).

The term "detectably labeled" encompasses labels that can be directly or indirectly detected.

Directly detectable labels either provide a detectable signal or they interact with a second label to modify the detectable signal provided by the first or second label, e.g. to give FRET (fluorescence resonance energy transfer). Labels such as fluorescent dyes and luminescent (including chemiluminescent and electrochemiluminescent) dyes (Briggs et al "Synthesis of Functionalised Fluorescent Dyes and Their Coupling to Amines and Amino Acids," J. Chem. Soc., Perkin-Trans. 1 (1997) 1051-1058) provide a detectable signal and are generally applicable for labeling. In one embodiment detectably labeled refers to a label providing or inducible to provide a detectable signal, i.e. to a fluorescent label, to a luminescent label (e.g. a chemiluminescent label or an electrochemiluminescent label), a radioactive label or a metal-chelate based label, respectively.

Numerous labels (also referred to as dyes) are available which can be generally grouped into the following categories, all of them together and each of them representing embodiments according to the present disclosure:

(a) Fluorescent Dyes

Fluorescent dyes are e.g. described by Briggs et al "Synthesis of Functionalized Fluorescent Dyes and Their Coupling to Amines and Amino Acids," J. Chem. Soc., Perkin-Trans. 1 (1997) 1051-1058).

Fluorescent labels or fluorophores include rare earth chelates (europium chelates), fluorescein type labels including FITC, 5-carboxyfluorescein, 6-carboxy fluorescein; rhodamine type labels including TAMRA; dansyl; Lissamine; cyanines; phycoerythrins; Texas Red; and analogs thereof. The fluorescent labels can be conjugated to an aldehyde group comprised in target molecule using the techniques disclosed herein. Fluorescent dyes and fluorescent label reagents include those which are commercially available from Invitrogen/Molecular Probes (Eugene, Oregon, USA) and Pierce Biotechnology, Inc. (Rockford, Ill.).

(b) Luminescent Dyes

Luminescent dyes or labels can be further subcategorized into chemiluminescent and electrochemiluminescent dyes.

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 2000; 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru (Bpy)3]2+ (which releases a photon at ~620 nm) regenerating with TPA (Tripropylamine) in liquid phase or liquid-solid interface are used as ECL-labels.

Electrochemiluminescent (ECL) assays provide a sensitive and precise measurement of the presence and concentration of an analyte of interest. Such techniques use labels or other reactants that can be induced to luminesce when electrochemically oxidized or reduced in an appropriate chemical environment. Such electrochemiluminescense is triggered by a voltage imposed on a working electrode at a particular time and in a particular manner. The light produced by the label is measured and indicates the presence or quantity of the analyte. For a fuller description of such ECL techniques, reference is made to U.S. Pat. Nos. 5,221,605, 5,591,581, 5,597,910, PCT published application WO90/05296, PCT published application WO92/14139, PCT published application WO90/05301, PCT published application WO96/24690, PCT published application US95/03190, PCT application US97/16942, PCT published application US96/06763, PCT published application WO95/08644, PCT published application WO96/06946, PCT published application WO96/33411, PCT published application WO87/06706, PCT published application WO96/39534, PCT published application WO96/41175, PCT published application WO96/40978, PCT/US97/03653 and U.S. patent application Ser. No. 08/437,348 (U.S. Pat. No. 5,679,519). Reference is also made to a 1994 review of the analytical applications of ECL by Knight, et al. (Analyst, 1994, 119: 879-890) and the references cited therein. In one embodiment the method according to the present description is practiced using an electrochemiluminescent label.

Recently also Iridium-based ECL-labels have been described (WO2012107419).

(c) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(d) Metal-chelate complexes suitable as labels for imaging and therapeutic purposes are well-known in the art (US 2010/0111861; U.S. Pat. Nos. 5,342,606; 5,428,155; 5,316, 757; 5,480,990; 5,462,725; 5,428,139; 5,385,893; 5,739, 294; 5,750,660; 5,834,461; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al, J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

EMBODIMENTS

In a first aspect, the present invention relates to a method of assessing whether a patient has endometriosis or is at risk of developing endometriosis, comprising a) determining the amount of S100A8 in a sample of the patient, and b) comparing the determined amount to a reference.

In embodiments, an elevated amount of S100A8 in the sample of the patient is indicative of the presence or the risk of developing endometriosis in the patient. In particular, an amount of S100A8 in the sample of the patient is indicative of the presence or the risk of developing of endometriosis in the patient if the amount of S100A8 in the sample of the patient is higher than the amount of S100A8 in a reference or reference sample. In particular, S100A8 is detectable in higher amounts in a fluid sample of the patient assessed for the presence or risk of developing endometriosis than in the same fluid sample of individuals not suffering or being at risk of developing endometriosis.

In particular, an amount of S100A8 elevated by 50% or more, is indicative of the presence or the risk of developing of endometriosis. In particular, an amount of S100A8 elevated by 100% or more, is indicative of the presence or the risk of developing of endometriosis. In particular, an amount of S100A8 elevated by 150% or more, is indicative of the presence or the risk of developing of endometriosis. In particular, an amount of S100A8 elevated by 200% or more, is indicative of the presence or the risk of developing of endometriosis.

In embodiments, the sample of the patient is body fluid sample. In particular embodiments, the sample is a whole blood, serum or plasma sample. In embodiments, the sample is an in vitro sample, i.e. it will be analyzed in vitro and not transferred back into the body.

In particular embodiments, the patient is a laboratory animal, a domestic animal or a primate. In particular embodiments, the patient is a human patient. In particular embodiments, the patient is a female human patient.

In embodiments, the endometriosis assessed is selected from the group consisting of stage I endometriosis according to rASRM staging, stage II endometriosis according to rASRM staging, stage III endometriosis according to rASRM staging, stage IV endometriosis according to rASRM staging. In particular embodiments, the endometriosis assessed is stage I, stage II, stage III, or stage IV endometriosis. In embodiments, endometriosis is early endometriosis, in particular stage I endometriosis according to rASRM staging or stage II endometriosis according to rASRM staging. In particular embodiments, the endometriosis assessed is stage III or stage IV endometriosis.

In embodiments, the endometriosis assessed is selected from the group consisting of peritoneal endometriosis, endometrioma, deep infiltrating endometriosis (DIE), and adenomyosis.

In particular embodiments, the endometriosis assessed is peritoneal endometriosis of stage I or II according to rASRM staging.

In embodiments, the assessment is performed independent of the rASRM staging. In particular, the assessment is performed without performing laparoscopy. In particular the assessment is performed without assessing the presence or severity of endometriosis in the patient using laparoscopy and/or the rASRM staging.

In embodiment, the method of the present invention is an in vitro method.

In embodiments, the amount of S100A8 is determined using antibodies, in particular using monoclonal antibodies. In embodiments, step a) of determining the amount of S100A8 in a sample of the patient comprises performing an immunoassay. In embodiments, the immunoassay is performed either in a direct or indirect format. In embodiments such immunoassays is selected from the group consisting of enzyme linked immunosorbent assay (ELISA), enzyme immunoassay (EIA), radioimmunoassay (RIA), or immuno assays based on detection of luminescence, fluorescence, chemiluminescence or electrochemiluminescence.

In particular embodiments, step a) of determining the amount of S100A8 in a sample of the patient comprises the steps of
i) incubating the sample of the patient with one or more antibodies specifically binding to S100A8, thereby generating a complex between the antibody and S100A8, and
ii) quantifying the complex formed in step i), thereby quantifying the amount of S100A8 in the sample of the patient.

In particular embodiments, in step i) the sample is incubated with two antibodies, specifically binding to S100A8. As obvious to the skilled artisan, the sample can be contacted with the first and the second antibody in any desired order, i.e. first antibody first and then the second antibody or second antibody first and then the first antibody, or simultaneously, for a time and under conditions sufficient to form a first anti-S100A8 antibody/S100A8/second anti-S100A8 antibody complex. As the skilled artisan will readily appreciate it is nothing but routine experimentation to establish the time and conditions that are appropriate or that are sufficient for the formation of a complex either between the specific anti-S100A8 antibody and the S100A8 antigen/analyte (=anti-S100A8 complex) or the formation of the secondary, or sandwich complex comprising the first antibody to S100A8, S100A8 (the analyte) and the second anti-S100A8 antibody (=anti-S100A8 antibody/S100A8/second anti-S100A8 antibody complex).

The detection of the anti-S100A8 antibody/S100A8 complex can be performed by any appropriate means. The detection of the first anti-S100A8 antibody/S100A8/second anti-S100A8 antibody complex can be performed by any appropriate means. The person skilled in the art is absolutely familiar with such means/methods.

In certain embodiments a sandwich will be formed comprising a first antibody to S100A8, S100A8 (analyte) and the second antibody to S100A8, wherein the second antibody is detectably labeled.

In one embodiment a sandwich will be formed comprising a first antibody to S100A8, the S100A8 (analyte) and the second antibody to S100A8, wherein the second antibody is detectably labeled and wherein the first anti-S100A8 antibody is capable of binding to a solid phase or is bound to a solid phase.

In embodiments, the second antibody is directly or indirectly detectably labeled. In particular embodiments, the second antibody is detectably labeled with a luminescent dye, in particular a chemiluminescent dye or an electrochemiluminescent dye.

In embodiments, the method further comprising the assessment of the presence of dysmenorrhea and/or lower abdominal pain in the patient. In embodiments the presence of dysmenorrhea and/or lower abdominal pain is assessed according to the VAS scale. In embodiments, dysmenorrhea VAS score of 4 or higher indicated moderate or severe dysmenorrhea. In embodiments, scores of 3 or less indicate no or mild dysmenorrhea. In embodiments, the method further comprising determining the amount or concentration of CA-125.

In embodiments, the method comprising calculating a ratio of the amount or concentration of S100A8 and dysmenorrhea, of the amount or concentration of S100A8 and lower abdominal pain according to the VAS scale, or the amount or concentration of S100A8 and the amount or concentration of CA-125.

In a second aspect, the present invention relates to a method of selecting a patient for therapy of endometriosis, comprising a) determining the amount or concentration of S100A8 in a sample of the patient, and b) comparing the determined amount or concentration to a reference.

In embodiments, a patient is selected for therapy of endometriosis if an elevated amount of S100A8 in the sample of the patient is determined. In particular, a patient is selected for therapy of endometriosis if the amount of S100A8 in the sample of the patient is higher than the amount of S100A8 in a reference or reference sample. In particular, a patient is selected for therapy of endometriosis if the amount of S100A8 is higher in a fluid sample of the patient assessed than in the same fluid sample of individuals not suffering or being at risk of developing endometriosis or not being selected for therapy of endometriosis.

In particular, a patient is selected for therapy of endometriosis if the amount of S100A8 is elevated by 50% or more. In particular, a patient is selected for therapy of endometriosis if the amount of S100A8 is elevated by 100% or more. In particular, a patient is selected for therapy of endometriosis if the amount of S100A8 is elevated by 150% or more. In particular, a patient is selected for therapy of endometriosis if the amount of S100A8 is elevated by 200% or more.

In embodiments, the patient is selected for a therapy of endometriosis selected from the group consisting of drug-based therapy or surgical therapy. In embodiments surgical therapy of endometriosis is laparoscopy or nerve sparing surgery. In embodiments drug-based therapy of endometriosis is inhibiting or targeting neurogenic inflammation and/or pain medication and/or hormonal therapy (e.g. hormonal contraceptives or GnRH agonists).

In embodiments, the sample of the patient is body fluid sample. In particular embodiments, the sample is a whole blood, serum or plasma sample. In embodiments, the sample is an in vitro sample, i.e. it will be analyzed in vitro and not transferred back into the body.

In particular embodiments, the patient is a laboratory animal, a domestic animal or a primate. In particular embodiments, the patient is a human patient. In particular embodiments, the patient is a female human patient.

In embodiments, the endometriosis is selected from the group consisting of stage I endometriosis according to rASRM staging, stage II endometriosis according to rASRM staging, stage III endometriosis according to rASRM staging, stage IV endometriosis according to rASRM staging. In particular embodiments, the endometriosis is stage I, stage II, stage III, or stage IV endometriosis. In embodiments, endometriosis is early endometriosis, in particular stage I endometriosis according to rASRM staging or stage II endometriosis according to rASRM staging. In particular embodiments, the endometriosis assessed is stage III or stage IV endometriosis.

In embodiments, the endometriosis is selected from the group consisting of peritoneal endometriosis, endo-metrioma, deep infiltrating endometriosis (DIE), and adeno-myosis.

In particular embodiments, the endometriosis assessed is peritoneal endometriosis of stage I or II according to rASRM staging.

In embodiment, the method of the present invention is an in vitro method.

In embodiments, the amount of S100A8 is determined using antibodies, in particular using monoclonal antibodies.

In embodiments, step a) of determining the amount of S100A8 in a sample of the patient comprises performing an immunoassay. In embodiments, the immunoassay is performed either in a direct or indirect format. In embodiments such immunoassays is selected from the group consisting of enzyme linked immunosorbent assay (ELISA), enzyme immunoassay (EIA), radioimmunoassay (RIA), or immuno assays based on detection of luminescence, fluorescence, chemiluminescence or electrochemiluminescence.

In particular embodiments, step a) of determining the amount of S100A8 in a sample of the patient comprises the steps of i) incubating the sample of the patient with one or more antibodies specifically binding to S100A8, thereby generating a complex between the antibody and S100A8, and ii) quantifying the complex formed in step i), thereby quantifying the amount of S100A8 in the sample of the patient.

In particular embodiments, in step i) the sample is incubated with two antibodies, specifically binding to S100A8. As obvious to the skilled artisan, the sample can be contacted with the first and the second antibody in any desired order, i.e. first antibody first and then the second antibody or second antibody first and then the first antibody, or simultaneously, for a time and under conditions sufficient to form a first anti-S100A8 antibody/S100A8/second anti-S100A8 antibody complex. As the skilled artisan will readily appreciate it is nothing but routine experimentation to establish the time and conditions that are appropriate or that are sufficient for the formation of a complex either between the specific anti-S100A8 antibody and the S100A8 antigen/analyte (=anti-S100A8 complex) or the formation of the secondary, or sandwich complex comprising the first antibody to S100A8, S100A8 (the analyte) and the second anti-S100A8 antibody (=anti-5100A8 antibody/S100A8/second anti-5100A8 antibody complex). The detection of the anti-S100A8 antibody/S100A8 complex can be performed by any appropriate means. The detection of the first anti-S100A8 antibody/S100A8/second anti-S100A8 antibody complex can be performed by any appropriate means. The person skilled in the art is absolutely familiar with such means/methods.

In certain embodiments, a sandwich will be formed comprising a first antibody to S100A8, S100A8 (analyte) and the second antibody to S100A8, wherein the second antibody is detectably labeled.

In one embodiment a sandwich will be formed comprising a first antibody to S100A8, the S100A8 (analyte) and the second antibody to S100A8, wherein the second antibody is detectably labeled and wherein the first anti-S100A8 antibody is capable of binding to a solid phase or is bound to a solid phase.

In embodiments, the second antibody is directly or indirectly detectably labeled. In particular embodiments, the second antibody is detectably labeled with a luminescent dye, in particular a chemiluminescent dye or an electrochemiluminescent dye.

In embodiments, the method further comprising the assessment of the presence of dysmenorrhea and/or lower abdominal pain in the patient. In embodiments the presence of dysmenorrhea and/or lower abdominal pain is assessed according to the VAS scale. In embodiments, dysmenorrhea VAS score of 4 or higher indicated moderate or severe dysmenorrhea. In embodiments, scores of 3 or less indicate no or mild dysmenorrhea.

In embodiments, the method further comprising determining the amount or concentration of CA-125.

In embodiments, the method comprising calculating a ratio of the amount or concentration of S100A8 and dysmenorrhea, of the amount or concentration of S100A8 and lower abdominal pain according to the VAS scale, or the amount or concentration of S100A8 and the amount or concentration of CA-125.

In a third aspect, the present invention relates to a method of monitoring a patient suffering from endometriosis or being treated for endometriosis, comprising a) determining the amount or concentration of S100A8 in a sample of the patient, and b) comparing the determined amount or concentration to a reference.

In embodiments, a patient suffering from endometriosis is monitored to determine if the amount or concentration of S100A8 is changing over time in a sample of the patient. In particular, a patient suffering from endometriosis is monitored to determine if the amount or concentration of S100A8 is increasing, decreasing or not changing over time. In embodiments, a patient suffering from endometriosis is monitored if an elevated amount of S100A8 in the sample of the patient is determined.

In embodiments, a patient being treated for endometriosis is monitored to determine if the amount or concentration of S100A8 is changing in a sample of the patient. In particular, a patient being treated for endometriosis is monitored to determine if the amount or concentration of S100A8 is increasing, decreasing or not changing. In particular, a patient being treated for endometriosis is monitored to determine if the amount or concentration of S100A8 is increasing, decreasing or not changing due to the therapy applied. In embodiments, a decreasing amount or concentration of S100A8 in a patient being treated for endometriosis is indicative of the therapy being effective. In embodiments, an unaltered or increasing amount or concentration of S100A8 in a sample of the patient being treated for endometriosis is indicative of the therapy being ineffective, i.e. an unaltered or increasing amount or concentration of S100A8 in a sample of the patient being treated for endometriosis is indicative of persisting or recurring endometriosis. In particular, the treatment for endometriosis is ineffective if the amount of S100A8 is increasing to 50% or more. In particular, the treatment for endometriosis is ineffective if the amount of S100A8 is increasing to 100% or more. In particular, the treatment for endometriosis is ineffective if the amount of S100A8 is increasing to 150% or more. In particular, the treatment for endometriosis is ineffective if the amount of S100A8 is increasing to 200% or more.

In particular embodiments, therapy is adapted if an unaltered or increasing amount or concentration of S100A8 in a sample of the patient being treated for endometriosis is determined.

In embodiments, the patient is monitored several times at different time points. In embodiments, the patient is monitored several times within a time frame of weeks, months or years. In particular embodiments, a patient is monitored is once a months or once a year. In embodiments, a patient suffering from endometriosis is monitored once a months or once a year after diagnosis of endometriosis. In embodiments, a patient being treated for endometriosis is monitored once after therapy, in particular once after surgical therapy. In particular, the patient being treated for endometriosis is monitored once a months or once a year to determine the efficacy of treatment and/or the recurrence of endometriosis.

In embodiments, therapy of endometriosis is selected from the group consisting of drug-based therapy or surgical therapy. In embodiments, surgical therapy of endometriosis is laparoscopy or nerve sparing surgery. In embodiments, drug-based therapy of endometriosis is inhibiting or targeting neurogenic inflammation and/or pain medication and/or hormonal therapy. In embodiments, the sample of the patient is body fluid sample. In particular embodiments, the sample is a whole blood, serum or plasma sample. In embodiments, the sample is an in vitro sample, i.e. it will be analyzed in vitro and not transferred back into the body.

In particular embodiments, the patient is a laboratory animal, a domestic animal or a primate. In particular embodiments, the patient is a human patient. In particular embodiments, the patient is a female human patient.

In embodiments, the endometriosis is selected from the group consisting of stage I endometriosis according to rASRM staging, stage II endometriosis according to rASRM staging, stage III endometriosis according to rASRM staging, stage IV endometriosis according to rASRM staging. In particular embodiments, the endometriosis is stage I, stage II, stage III, or stage IV endometriosis. In embodiments, endometriosis is early endometriosis, in particular stage I endometriosis according to rASRM staging or stage II endometriosis according to rASRM staging. In particular embodiments, the endometriosis assessed is stage III or stage IV endometriosis.

In embodiments, the endometriosis is selected from the group consisting of peritoneal endometriosis, endometrioma, deep infiltrating endometriosis (DIE), and adenomyosis.

In particular embodiments, the endometriosis assessed is peritoneal endometriosis of atge I or II according to rASRM staging.

In embodiment, the method of the present invention is an in vitro method.

In embodiments, the amount of S100A8 is determined using antibodies, in particular using monoclonal antibodies. In embodiments, step a) of determining the amount of S100A8 in a sample of the patient comprises performing an immunoassay. In embodiments, the immunoassay is performed either in a direct or indirect format. In embodiments such immunoassays is selected from the group consisting of enzyme linked immunosorbent assay (ELISA), enzyme immunoassay (EIA), radioimmunoassay (RIA), or immuno assays based on detection of luminescence, fluorescence, chemiluminescence or electrochemiluminescence.

In particular embodiments, step a) of determining the amount of S100A8 in a sample of the patient comprises the steps of i) incubating the sample of the patient with one or more antibodies specifically binding to S100A8, thereby generating a complex between the antibody and S100A8, and ii) quantifying the complex formed in step i), thereby quantifying the amount of S100A8 in the sample of the patient.

In particular embodiments, in step i) the sample is incubated with two antibodies, specifically binding to S100A8. As obvious to the skilled artisan, the sample can be contacted with the first and the second antibody in any desired order, i.e. first antibody first and then the second antibody or second antibody first and then the first antibody, or simultaneously, for a time and under conditions sufficient to form a first anti-S100A8 antibody/S100A8/second anti-S100A8 antibody complex. As the skilled artisan will readily appreciate it is nothing but routine experimentation to establish the time and conditions that are appropriate or that are sufficient for the formation of a complex either between the specific anti-S100A8 antibody and the S100A8 antigen/analyte (=anti-S100A8 complex) or the formation of the secondary, or sandwich complex comprising the first antibody to S100A8, S100A8 (the analyte) and the second anti-S100A8 antibody (=anti-5100A8 antibody/S100A8/second anti-S100A8 antibody complex).

The detection of the anti-S100A8 antibody/S100A8 complex can be performed by any appropriate means. The detection of the first anti-S100A8 antibody/S100A8/second anti-S100A8 antibody complex can be performed by any appropriate means. The person skilled in the art is absolutely familiar with such means/methods.

In certain embodiments, a sandwich will be formed comprising a first antibody to S100A8, S100A8 (analyte) and the second antibody to S100A8, wherein the second antibody is detectably labeled.

In one embodiment a sandwich will be formed comprising a first antibody to S100A8, the S100A8 (analyte) and the second antibody to S100A8, wherein the second antibody is detectably labeled and wherein the first anti-S100A8 antibody is capable of binding to a solid phase or is bound to a solid phase.

In embodiments, the second antibody is directly or indirectly detectably labeled. In particular embodiments, the second antibody is detectably labeled with a luminescent dye, in particular a chemiluminescent dye or an electrochemiluminescent dye.

In embodiments, the method further comprising the assessment of the presence of dysmenorrhea and/or lower abdominal pain in the patient. In embodiments the presence of dysmenorrhea and/or lower abdominal pain is assessed according to the VAS scale. In embodiments, dysmenorrhea VAS score of 4 or higher indicated moderate or severe dysmenorrhea. In embodiments, scores of 3 or less indicate no or mild dysmenorrhea.

In embodiments, the method further comprising determining the amount or concentration of CA-125.

In embodiments, the method comprising calculating a ratio of the amount or concentration of S100A8 and dysmenorrhea, of the amount or concentration of S100A8 and lower abdominal pain according to the VAS scale, or the amount or concentration of S100A8 and the amount or concentration of CA-125.

In further embodiments, the present invention relates to the following aspects:

1. Method of assessing whether a patient has endometriosis or is at risk of developing endometriosis, comprising
   determining the amount or concentration of S100A8 in a sample of the patient, and
   comparing the determined amount or concentration to a reference.
2. Method of selecting a patient for therapy (in particular drug-based therapy or surgical therapy (laparoscopy) of endometriosis, comprising
   determining the amount or concentration of S100A8 in a sample of the patient, and
   comparing the determined amount or concentration to a reference.
3. Method of monitoring a patient suffering from endometriosis or being treated for endometriosis, comprising
   determining the amount or concentration of S100A8 in a sample of the patient, and comparing the determined amount or concentration to a reference.
4. The method of aspects 1 to 3, wherein an elevated amount or concentration of S100A8 in the sample of the patient is indicative of the presence of endometriosis in the patient.
5. The method of aspects 1 to 4, wherein the sample is body fluid.
6. The method of aspects 1 to 5, wherein the sample is blood, serum or plasma.
7. The method of aspects 1 to 6, wherein the subject is a female patient, in particular a human female patient.
8. The method of aspects 1 to 7, wherein the assessment is performed independent of the rASRM staging.
9. The method of aspects 1 to 8, wherein endometriosis is selected from the group consisting of stage I endometriosis according to rASRM staging, stage II endometriosis according to rASRM staging, stage III endometriosis according to rASRM staging, stage IV endometriosis according to rASRM staging.
10. The method of aspects 1 to 9, wherein endometriosis is early endometriosis, in particular stage I endometriosis according to rASRM staging or stage II endometriosis according to rASRM staging.
11. The method of aspects 1 to 10, wherein endometriosis is selected from the group consisting of peritoneal endometriosis, endometrioma, deep infiltrating endometriosis, and adenomyosis.
12. The method of aspects 1 to 11, further comprising the assessment of dysmenorrhea according to the VAS scale and/or lower abdominal pain according to the VAS scale.
13. The method of aspects 1 to 12, further comprising determining the amount or concentration of CA-125.
14. The method of aspects 12 or 13, comprising calculating a ratio of the amount or concentration of S100A8 and dysmenorrhea, of the amount or concentration of S100A8 and lower abdominal pain according to the VAS scale, or the amount or concentration of S100A8 and the amount or concentration of CA-125.

The following examples and figures are provided to aid the understanding of the present invention, the true scope of which is set forth in the appended claims. It is understood that modifications can be made in the procedures set forth without departing from the spirit of the invention.

EXAMPLES

Example 1: Diagnostic Performance of Biomarker S100A8 and Biomarker Combinations in Women with Endometriosis and Controls For the measurements, a total of 21 serum as well as 31 plasma samples from human females were analysed. The concentration of the analytes was determined by ELISA (enzyme-linked immunosorbent assay). The case group is comprised of patients diagnosed with pelvic endometriosis (ASRM stages I-IV) diagnosed by laparoscopic visualization with subsequent histological confirmation and the control group comprising healthy women without endometriosis.

The concentration of S100A8 in human serum was determined using the Human S100A8/MRP8 ELISA kit from CircuLex/MBL (distributed by Biozol Eching, Germany; catalogue number: CY-8061). The kit utilizes the quantitative sandwich ELISA technique. The measurement range for this assay is 78.1 pg/mL-5,000 pg/mL. Microtiter plates are pre-coated with a monoclonal antibody specific for human S100A8. Samples are measured in a 200-fold dilution. After bringing all reagents to room temperature, 100 µL of each sample and standard are added. Samples are measured in singlicates, standards in duplicates. During 1 h incubation at room temperature on a microplate shaker set to 650 rounds per minute (rpm), any S100A8 present is bound to the immobilized capture antibody on the microtiter plate. During washing step (4×350 µL), unbound substances are removed from the plate before 100 µL of an enzyme-linked monoclonal antibody specific for S100A8 is added to the wells. Following 1 h incubation on a shaker and another washing step to remove any unbound detection antibody, 100 µL of substrate solution is added to the plate. Within the next 10 min, the color develops in proportion to the amount of S100A8 bound in the initial step. Color development is stopped by addition of 100 µL stop solution and colour intensity is measured with a plate reader at 450 nm for detection and 570 nm for background subtraction. For generation of calibrator curves, lyophilized, recombinant S100A8 delivered with the kit was reconstituted and diluted in calibrator diluent. The calibration range of the assay is 78.1 pg/mL-5,000 pg/mL. Calibrator 6 (5,000 pg/mL) is prepared by reconstitution of the Human S100A8 Standard (provided in the kit) with 400 µL of dilution buffer further dilution 1:10. Calibrator 5 to calibrator 1 (78.1 pg/mL) are prepared by serial 2-fold dilution steps in calibrator diluent. Pure calibrator diluent serves as blank (0 pg/mL). The calibration curves were fitted using a 4-parameter nonlinear regression (Newton/Raphson) with no weighting.

The concentration of CA-125 was determined by a cobas e 601 analyzer. Detection of CA 125 II with a cobas e 601 analyzer is based on the Elecsys® ElectroChemiLumines-cence (ECL) technology. In brief, biotin-labelled and ruthenium-labelled antibodies are combined with the respective amount of undiluted sample and incubated on the analyzer. Subsequently, streptavidin-coated magnetic microparticles are added and incubated on the instrument in order to facilitate binding of the biotin-labelled immunological complexes. After this incubation step the reaction mixture is transferred into the measuring cell where the beads are magnetically captured on the surface of an electrode. Pro-Cell M Buffer containing tripropylamine (TPA) for the subsequent ECL reaction is then introduced into the measuring cell in order to separate bound immunoassay complexes from the free remaining particles. Induction of voltage between the working and the counter electrode then initiates the reaction leading to emission of photons by the ruthenium complexes as well as TPA. The resulting electrochemiluminescent signal is recorded by a photomultiplier and converted into numeric values indicating concentration level of the respective analyte.

Receiver Operating Characteristic (ROC) curves were generated (see FIGS. 1A-1C for single biomarkers and FIG. 2 for combination of biomarkers and clinical symptoms). The model performance is determined by looking at the area under the curve (AUC). The best possible AUC is 1 while the lowest possible is 0.5. Optimal cut-offs were selected using Youden's index (maximized sum of sensitivity plus specificity−1).

TABLE 1

Diagnostic performance of biomarker S100A8 and biomarker combinations in women with endometriosis and controls

| Biomarker | AUC | 95% CI (confidence interval) | N (sample size) | Sample type |
|---|---|---|---|---|
| S100A8 | 0.8200 | 0.6524 0.9876 | 25 | Serum |
| CA-125 | 0.6700 | 0.5136 0.8264 | 51 | Serum/Plasma |
| Dysmenorrhea | 0.6118 | 0.3829 0.8406 | 27 | Serum/Plasma |
| S100A8 + Dysmenorrhea | 0.8625 | 0.6923 1.0000 | 18 | Serum |

For the multivariate analysis, AUC plots, a cut-off for the combination of the different biomarkers was applied to predict endometriosis based on multivariable logistic regression analysis and Youden's index. A dysmenorrhea VAS score of 4 or higher indicated moderate or severe dysmenorrhea. Scores of 3 or less indicate no or mild dysmenorrhea.

TABLE 2

Cut-off for combination of various biomarker to predict endometriosis based on multivariable logistic regression analysis and Youden's index.

| Intercept $\alpha^*$ | S100A8 $\beta_1$ ** | Dysmenorrhea VAS $\beta_2$ ** | Cut-off (logit) for Endometriosis |
|---|---|---|---|
| −3.1470 | 0.000034 | −0.8672 | ≥−0.58422 |

*Intercept $\alpha$: The point where the curve crosses the y axis;
** Parameter $\beta$: The slope of the linear regression curve for each variable.

The values of parameters a and 13 vary depending on the analytes and clinical symptom included in the multivariate analysis, respectively.
Multivariable Logistic Regression Model with S100A8 and Dysmenorrhea VAS:

If logit=$\alpha$+($\beta$1*S100A8 value[pg/mL])+ ($\beta$2*Dysmenorrhea value [VAS])≥cut-off then disease (i.e. Endometriosis Stage I, II, III or IV) else no disease or If logit=−3.1474+(0.000033*S100A8)+(−0.8672*dysmenorrhea value)≥−0.58422, then disease (i.e. Endometriosis Stage I, II, III or IV), else no disease Box plots (see FIGS. 3A & 3B) were generated for endometriosis cases/controls (FIG. 3A) and endometriosis cases G1/2 (rASRM Stage I-II)/endometriosis cases G3-4 (rASRM Stage III-IV)/controls (FIG. 3B). The data are presented using box and whisker plots, including the median (middle quartile), the interquartile range (which represents the middle 50% of scores for the group), the upper quartile (75% of scores fall below the upper quartile), the lower quartile (25% of scores fall below the lower quartile). The whiskers show the 5th percentile and the 95th percentile respectively.

Example 2 Diagnostic Performance of Biomarker S100A8 and Biomarker Combinations in Women with Adenomyosis and Controls The case group is comprised of patients diagnosed with adenomyosis by laparoscopic visualization with subsequent histological confirmation and the control group includes healthy women without adenomyosis. Inclusion criteria for the case group were the presence of pelvic pain/infertility and age between 18-45 years. Exclusion criteria for the case group were pregnant/breastfeeding, malignancy, recurrent adenomyosis and laparoscopy/laparotomy≤6 months.

The concentration of S100A8 in human serum was determined using the Human S100A8/MR8 ELISA kit from CircuLex/MBL (for details, see Example 1 above).

The concentration of CA-125 was determined by a cobas e 601 analyzer using the Elecsys® CA 125 II as described earlier in example 1.

Receiver Operating Characteristic (ROC) curves were generated by univariate models for the single biomarkers. The model performance is determined by looking at the area under the curve (AUC).

TABLE 3

Diagnostic performance of single biomarkers S100A8 and CA-125 in adenomyosis cases and controls.

| Biomarker | AUC | p-value (Mann-Whitney test) | N (cases) | N (controls) |
|-----------|-----|-----------------------------|-----------|--------------|
| S100A8 | 0.69 (0.62-0.77) | 1.06e−05 | 109 | 72 |
| CA-125 | 0.6 (0.52-0.68) | 0.023 | 109 | 72 |

The diagnostic performance of S100A8 to distinguish adenomyosis cases versus controls is higher compared to the diagnostic performance of the biomarker CA-125.

FIGS. 4A & 4B. Box plots and ROC curves of serum levels of S100A8 in adenomyosis cases and controls. (FIG. 4A) The box plot shows serum S100A8 levels of controls versus adenomyosis cases. The lower and upper edges of each box correspond to the first and third quartile, respectively. The middle thick line represents the median value and the upper and lower whiskers represent values that are 1.5 times the interquartile range. (FIG. 4B) The ROC curve for serum S100A8 is shown for controls and adenomyosis cases.

FIGS. 5A & 5B. Box plots and ROC curves of serum levels of CA-125 in adenomyosis cases and controls. (FIG. 5A) The box plot shows serum CA-125 levels of controls versus adenomyosis cases. The lower and upper edges of each box correspond to the first and third quartile, respectively. The middle thick line represents the median value and the upper and lower whiskers represent values that are 1.5 times the interquartile range. (FIG. 5B) The ROC curve for serum CA-125 is shown for controls and adenomyosis cases.

The invention claimed is:

1. A non-invasive method of assessing whether a patient has endometriosis or is at risk of developing endometriosis, comprising
   measuring the amount or concentration of S100 calcium binding protein A8 (S100A8) in a sample of the patient, wherein the sample is a body fluid selected from the group consisting of blood, serum, and plasma, and
   comparing the measured amount or concentration to a reference,
   wherein the patient has stage I endometriosis according to revised American Society for Reproductive Medicine (rASRM) staging or stage II endometriosis according to rASRM staging, and
   administering a therapy for endometriosis to the patient, wherein the therapy is selected from the group consisting of a drug-based therapy, a surgical therapy, and a hormonal therapy.

2. A non-invasive method of selecting a patient for drug-based therapy or surgical therapy (laparoscopy) of endometriosis, comprising
   measuring the amount or concentration of S100A8 in a sample of the patient, wherein the sample is a body fluid selected from the group consisting of blood, serum, and plasma, and
   comparing the measured amount or concentration to a reference,
   wherein the patient is suspected of having or has stage I endometriosis according to rASRM staging or stage II endometriosis according to rASRM staging, and
   administering the drug-based therapy or performing the surgical therapy on the patient selected for therapy.

3. A non-invasive method of monitoring a patient suffering from endometriosis or being treated for endometriosis, comprising
   measuring the amount or concentration of S100A8 in a sample of the patient, wherein the sample is a body fluid selected from the group consisting of blood, serum, and plasma, and
   comparing the measured amount or concentration to a reference,
   wherein the patient is suspected of having or has stage I endometriosis according to rASRM staging or stage II endometriosis according to rASRM staging, and
   administering a therapy for endometriosis to the patient based on the monitoring, wherein the therapy is selected from the group consisting of a drug-based therapy, a surgical therapy, and a hormonal therapy.

4. The method of claim 1, wherein the patient is a human female patient.

5. The method of claim 1, wherein the assessment is performed independent of the rASRM staging.

6. The method of claim 1, wherein endometriosis is stage I endometriosis according to rASRM staging.

7. The method of claim 1, wherein endometriosis is stage II endometriosis according to rASRM staging.

8. The method of claim 1, wherein endometriosis is selected from the group consisting of peritoneal endometriosis, endometrioma, deep infiltrating endometriosis, and adenomyosis.

9. The method of claim 1, wherein adenomyosis is assessed.

10. The method of claim 1, further comprising measuring the amount or concentration of Carbohydrate antigen 125 (CA-125) in a sample of the patient.

11. The method of claim 1, further comprising calculating a ratio of the amount or concentration of S100A8 and dysmenorrhea and/or of the amount or concentration of S100A8 and lower abdominal pain according to the VAS scale.

12. The method of claim 10, further comprising calculating a ratio of the amount or concentration of S100A8 and the amount or concentration of CA-125.

13. A method of detecting S100A8 in a sample from a patient, the method comprising:
   obtaining the sample from the patient, wherein the sample is a body fluid selected from the group consisting of blood, serum, and plasma, and
   detecting whether S100A8 is present in the sample by contacting the sample with a binding agent and detecting the binding between S100A8 and the binding agent, wherein the binding agent is an antibody that specifically binds to S100A8, and wherein the patient is suspected of having or has stage I endometriosis according to rASRM staging or stage II endometriosis according to rASRM staging.

14. A method for measuring the amount of S100A8 in a sample from a patient, the method comprising:

obtaining the sample from the patient, wherein the sample is a body fluid selected from the group consisting of blood, serum, and plasma, measuring the amount of S100A8 in the sample of the patient, and contacting the sample, or a portion thereof, with an agent which specifically binds S100A8, wherein the agent is an antibody and wherein the patient is suspected of having or has stage I endometriosis according to rASRM staging or stage II endometriosis according to rASRM staging.

15. A non-invasive method of assessing whether a patient has endometriosis or is at risk of developing endometriosis, wherein the patient is suspected of having or has stage I endometriosis according to rASRM staging or stage II endometriosis according to rASRM staging, comprising measuring the amount or concentration of S100A8 in a sample of the patient, wherein the measuring comprises incubating the sample of the patient with one or more antibodies specifically binding to S100A8 thereby generating a complex between the one or more antibodies and S100A8, and quantifying the complex thereby quantifying the amount of S100A8 in the sample of the patient, comparing the measured amount or concentration to a reference, assessing whether the patient has endometriosis or is at risk of developing endometriosis, wherein the sample is a body fluid selected from the group consisting of blood, serum, and plasma, and administering a therapy for endometriosis to the patient, wherein the therapy is selected from the group consisting of a drug-based therapy, a surgical therapy, and a hormonal therapy.

16. The method of claim 15, wherein a sandwich complex is formed comprising a first antibody to S100A8, S100A8 (analyte) and the second antibody to S100A8, wherein the second antibody is detectably labeled.

17. The method of claim 16, wherein the second antibody is detectably labeled with a chemiluminescent dye or an electrochemiluminescent dye.

18. The method of claim 15, further comprising measuring an amount or concentration of CA-125 in a sample of the patient.

19. A non-invasive method of assessing whether a patient has endometriosis or is at risk of developing endometriosis, comprising measuring the amount or concentration of S100 calcium binding protein A8 (S100A8) in a sample of the patient, wherein the sample is a body fluid selected from the group consisting of blood, serum, and plasma, and comparing the measured amount or concentration to a reference, wherein the patient has stage I endometriosis according to revised American Society for Reproductive Medicine (rASRM) staging or stage II endometriosis according to rASRM staging, and administering a therapy for endometriosis to the patient, wherein the therapy is selected from the group consisting of a drug-based therapy, a surgical therapy, and a hormonal therapy.

20. The method of claim 19, wherein the patient has dysmenorrhea according to a Visual Analog Scale (VAS) scale and/or lower abdominal pain according to the VAS scale.

21. The method of claim 1, wherein the therapy is selected from the group consisting of laparoscopy, nerve sparing surgery, administering GnRH agonists to the patient, administering hormonal contraceptives to the patient, and administering pain medication to the patient.

22. The method of claim 2, wherein the surgical therapy is laparoscopy or wherein the drug-based therapy comprises administering GnRH agonists to the patient.

23. The method of claim 3, wherein the therapy is laparoscopy or comprises administering GnRH agonists to the patient.

24. The method of claim 15, wherein the therapy is laparoscopy or comprises administering GnRH agonists to the patient.

25. The method of claim 19, wherein the therapy is selected from the group consisting of laparoscopy, nerve sparing surgery, administering GnRH agonists to the patient, and administering hormonal contraceptives to the patient.

* * * * *